(12) United States Patent
Keck et al.

(10) Patent No.: US 6,803,194 B1
(45) Date of Patent: Oct. 12, 2004

(54) USE OF RIBOZYMES FOR FUNCTIONATING GENES

(75) Inventors: James G. Keck, Redwood City, CA (US); Justin G. P. Wong, Oakland, CA (US)

(73) Assignee: HK Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/601,970

(22) PCT Filed: Feb. 12, 1999

(86) PCT No.: PCT/US99/03166

§ 371 (c)(1),
(2), (4) Date: Aug. 9, 2000

(87) PCT Pub. No.: WO99/41371

PCT Pub. Date: Aug. 19, 1999

Related U.S. Application Data

(63) Continuation-in-part of application No. 09/023,992, filed on Feb. 13, 1998, now abandoned.

(51) Int. Cl.[7] .......................... C12Q 1/68; G01N 33/53
(52) U.S. Cl. .......................... 435/6; 435/7.1; 435/91.1; 435/91.31; 435/91.32; 435/91.33; 435/91.4; 435/325; 435/375; 435/455; 435/471
(58) Field of Search ........................ 435/6, 7.1, 91.1, 435/91.31, 91.4, 91.32, 91.33, 325, 375, 455, 471

(56) References Cited

U.S. PATENT DOCUMENTS

| | | | |
|---|---|---|---|
| 4,987,071 A | 1/1991 | Cech et al. | 435/91 |
| 5,037,746 A | 8/1991 | Cech et al. | 435/91 |
| 5,093,246 A | 3/1992 | Cech et al. | 435/91 |
| 5,116,742 A | 5/1992 | Cech et al. | 435/91 |
| 5,180,818 A | 1/1993 | Cech et al. | 536/23.1 |
| 5,190,931 A | 3/1993 | Inouye | 435/91 |
| 5,217,879 A | 6/1993 | Huang et al. | 435/69.1 |
| 5,217,889 A | 6/1993 | Roninson et al. | 435/172.3 |
| 5,272,065 A | 12/1993 | Inouye et al. | 435/91.1 |
| 5,354,678 A | 10/1994 | Lebkowski et al. | 435/172.3 |
| 5,354,855 A | 10/1994 | Cech et al. | 536/24.1 |
| 5,457,281 A | 10/1995 | Bridges et al. | 800/205 |
| 5,496,698 A * | 3/1996 | Draper et al. | 435/6 |
| 5,504,200 A | 4/1996 | Hall et al. | 536/24.1 |
| 5,589,362 A | 12/1996 | Bujard et al. | 435/69.1 |
| 5,591,610 A | 1/1997 | Cech et al. | 435/91.31 |
| 5,599,706 A | 2/1997 | Stinchcomb et al. | 436/366 |
| 5,631,236 A | 5/1997 | Woo et al. | 514/44 |
| 5,667,969 A | 9/1997 | Sullenger et al. | 435/6 |
| 5,670,488 A | 9/1997 | Gregory et al. | 514/44 |
| 5,679,523 A | 10/1997 | Li et al. | 435/6 |
| 5,686,279 A | 11/1997 | Finer et al. | 435/172.3 |
| 5,837,531 A | 11/1998 | Dedieu et al. | 425/320.1 |
| 5,856,188 A | 1/1999 | Hampel et al. | 435/375 |
| 6,025,192 A | 2/2000 | Beach et al. | 435/320.1 |
| 6,040,174 A | 3/2000 | Imler et al. | 435/325 |
| 6,130,092 A | 10/2000 | Lieber et al. | 435/489 |
| 6,133,028 A | 10/2000 | Imler et al. | 435/325 |
| 6,204,052 B1 | 3/2001 | Bout et al. | 435/320.1 |
| 6,255,071 B1 | 7/2001 | Beach et al. | 435/69.1 |
| 6,391,311 B1 | 5/2002 | Ferrara et al. | 424/198.1 |
| 6,410,011 B1 | 6/2002 | Branellec et al. | 424/93.2 |
| 6,455,283 B1 | 9/2002 | Ferrara et al. | 435/69.4 |
| 2002/0094324 A1 | 7/2002 | Branellec et al. | 424/93.2 |

FOREIGN PATENT DOCUMENTS

| | | |
|---|---|---|
| DE | 4424762 | 7/1995 |
| EP | 0707071 | 4/1996 |
| GB | 2319773 | 6/1998 |
| WO | 9201786 | 2/1992 |
| WO | 9205286 | 4/1992 |
| WO | 9413833 | 6/1994 |
| WO | 9420618 | 9/1994 |
| WO | 9426877 | 11/1994 |
| WO | 9428152 | 12/1994 |
| WO | 9514091 | 5/1995 |
| WO | 9514101 | 5/1995 |
| WO | 9514102 | 5/1995 |
| WO | 9601314 | 1/1996 |
| WO | 9605321 | 2/1996 |
| WO | 9609392 | 3/1996 |

(List continued on next page.)

OTHER PUBLICATIONS

Zhao et al. Nature 365:448–451 (Sep. 1993).*
Bagnis et al., "Retroviral Transfer of the nlsLacZ Gene into Human CD34+Cell Populations and into TF–1 Cells: Future Prospects in Gene Therapy, " *Human Gene Therapy* 5:1325–33 (1994).
Doetschman et al., "Targeted mutation of the Hprt gene in mouse embryonic stem cells," *Proc. Natl. Acad. Sci. USA* 85:8583–8587 (1988).

(List continued on next page.)

*Primary Examiner*—Bennett Celsa
(74) *Attorney, Agent, or Firm*—Stephanie L. Seidman; Heller Ehrman White & McAuliffe, LLP

(57) ABSTRACT

Double stranded DNAs, expression vectors and methods for their use are provided in which the intracellular expression of the double stranded DNAs is used to alter the phenotype of a target cell so that the function of a target nucleic acid that includes a nucleotide sequence encoding a motif of interest can be determined using a combinatorial ribozyme library. The members of the library are catalytic RNAs that disrupt the expression of the transcription product of the target nucleic acid. Disruption of transcription product expression results in an altered cell phenotype which is used to determine the function of the target nucleic acid. The specific phenotype or response may be associated with normal cellular processes, or it may contribute to the generation of pathogenesis involved in disease development. The compositions find use in high-throughput screens to assign gene functions. When associated with a pathogenic phenotype, these genes or their gene products can constitute therapeutic targets for treatment of diseases. The complete sequence of the gene containing the target nucleic acid need not to be known for the method to be used successfully.

11 Claims, 6 Drawing Sheets

FOREIGN PATENT DOCUMENTS

| | | |
|---|---|---|
| WO | 9638553 | 12/1996 |
| WO | 9700326 | 1/1997 |
| WO | 9727212 | 7/1997 |
| WO | 9727213 | 7/1997 |
| WO | 9832880 | 7/1998 |
| WO | 9850530 | 11/1998 |
| WO | 02048403 | 6/2002 |

OTHER PUBLICATIONS

Re et al., "Nucleotide Sequences Responsible for Generation of Internally Deleted Sendai Virus Defective Interfering Genomes," *Virology* 146: 27–37 (1985).

Baldick et al. "Mutational analysis of the core, spacer, and initiator regions of vaccinia virus intermediate–class promoters." *J Virol* Aug.;66(8):4710–9 (1992).

Albert et al., "Antisense Knockouts: Molecular Scalpels for the Dissection of Signal Transduction", *Trends in Pharm Sci.*, 15:250–254, 1994.

Gewirtz et al., "Facilitating Oligonucleotide Delivery: Helping Antisense Deliver on its Promise", *Proc. Natl. Acad. Sci. USA*, 93:3161–3163, 1996.

Grassi et al., "Ribozymes: Structure, Function and Potential Therapy for Dominant Genetic Disorders", *Ann Med*, 28:499–510, 1996.

Merker et al., "The Protein Product of the Zebrafish Homologue of the Mouse T gene is Expressed in Nuclei of the Germ Ring and the Notochord of the Early Embryo", *Development*, 116:1021–1032, 1992.

Abraham et al., "Signal transduction through the T–Cell antigen receptor," *Trends in Biochemical Sciences* 17: 434–8 (1992).

Ausubel et al. (Eds.), *Current Protocols in Molecular Biology* New York: John Wiley & Sons, 1994.

Baier et al., "Construction and Characterization of ick–and fyn–Specific tRNA:Ribozyme Chimeras," *Molecular Immunology* 31(12): 923–932 (1994).

Bates et al., "Energy Coupling in *Escherichia coli* DNA Gyrase: the Relationship between Nucleotide Binding, Stand Passage, and DNA Supercoiling," *Biochemistry* 35:1408–16 (1996).

Bennett et al., "Selective cleavage of closely–related mRNAs by synthetic ribozymes," *Nucleic Acids Research* 20(4): 831–7 (1992).

Betrand et al., "Can hammerhead ribozymes be efficient tools to inactivate gene function", *Nucleic Acids Research* 22(d): 293–300 (1994).

Birikh et al., "The structure, function and application of the hammerhead ribozyme," *European Journal of Biochemistry* 245: 1–16 (1997).

Cameron, F. H. and P. A. Jennings, "Specific gene suppression by engineered ribozymes in monkey cells," *Proc. Natl. Acad. Sci. USA* 86: 9139–9143 (1989).

Cech, T. R., "Ribozyme engineering," *current Opinion in Structural Biology* 2: 605–9 (1992).

Chen et al. "Efficient hammerhead ribozyme and antisenses RNA targeting in a slow ribosome *Escherichia coli* mutant," *Nature Biotechnology* 15:432–5 (1997).

Chowrira et al., "In Vitro and In Vivo Comparison of Hammerhead, Hairpin, and Hepatitis Delta Virus Self–processing Ribozyme Cassettes," *J.Biol.Chem.* 269(41): 25856–64 (1994).

Cochran et al. "Eukaryotic transient expression system dependant on transcription factors and regulatory DNA sequences of vaccinia virus," *Proc. Natl. Acad. Sci. USA* 82:19–23 (1985).

Coffin et al. (Eds.) *Retroviruses* New York: Cold Spring Harbor Laboratory Press, 1997.

Couture, L. A. and D. T. Stinchcomb, "Anti–gene therapy: the use of ribozymes to inhibit gene function," *Trends in Genetics* 12(12): 510–5 (1996).

Danos, O. and R. C. Mulligan, "Safe and efficient generation of recombinant retroviruses with amphotropic and ecotropic host ranges," *Proc. Natl. Acad. Sci. USA* 85: 6460–4 (1988).

Derwent #010354638, WPI Acc. No.: 1995–255952/199534, for German Patent Publication DE 4424762 C and PCT patent Publication WO 9601314 A2, "Ribozyme library in optimised expression cassette—comprises central hammerhead region and variable flanking regions, allows selection of optium ribozyme for specific applications".

Derwent #010114899, WPI Acc. No.: 1995–016150/199503, for PCT Patent Publication WO 9428152 A1, "Non–replicating adenovirus derivs.—useful as vectors for exogenous genes".

Derwent #010305449, WPI Acc. No.: 1995–206709/199527, for PCT Patent Publication WO 9514101 A, "New recombinant adenovirus for gene therapy of cancer—contains heterologous sequence, e.g. for thymidine kinase or a ribozyme, controlled by sequences active specifically in tumour cells".

Derwent #010305450, WPI Acc. No.: 1995–206710/199527, for PCT Patent Publication WO 9514102 A, "New defective adenovirus contg. gene for thymidine kinase—useful in gene therapy for treating or preventing cancer or viral infection".

Derwent #010642759, WPI Acc. No.: 1996–139713/199614, for PCT Patent Publciation WO 9605321 A, "Use of defective, recombinant adenovirus carrying suicide gene—for gene therapy of restenosis by transferring selected genes to smooth muscle cells of atherosciertotic plaque".

Fedor, M.J. and O.C. Uhlenbeck, "Substrate sequence effectson "Hammerhead" RNA catalytic efficiency," *Proc. Natl. Acad. Sci. USA* 87: 1668–1672 (1990).

Feliciello, I. and G. Chinali, "A modified alkaline lysis method for the preparation of highly purified plasmid DNA from *Escherichia coli*," *analytical Biochemistry* 212: 394–401 (1993).

Finer et al., "kat: A High–Efficiency Retroviral Transduction System for Primary Human T Lymphocytes," *Blood* 83:(1): 43–50 (1994).

Forster, A.C. and S. Altman, "External Guide Sequences for an RNA enzyme," *Science* 249: 783–6 (1990).

Gibson, S.A. and E.J. Shillitoe, "Ribozymes," *Molecular Biotechnology* 7: 125–37 (1997).

Goldsmith, M.A. and A. Weiss, "Isolation and characterization of a T–lymphocyte somatic mutant with altered signal transduction by the antigen receptor," *Proc. Natl. Acad. Sci. USA* 84: 6879–83 (1987).

Hahn et al., "Infectious Sindbis virus transient expression vectors for studying antigen processing and presentation," *Proc. Natl. Acad. Sci. USA* 89: 2679–83 (1992).

Halbert et al., "Transduction by Adeno–Associated Virus Vectors in the Rabbit Airway: Efficiency, Persistance, and Readminisration," *Journal of Virolog* 71(8): 5932–41 (1997).

Hall et al., "An approach to High–Throughput Genotyping," *Genome Research* 6: 781–90 (1996).

Haseloff J. and W.L. Gerlach, "Simple RNA enzymes with new end highly specific endoribonuclease activities," *Nature* 334: 85–91 (1988).

Hofmann et al. "Rapid retroviral delivery of tetracycline–inducible genes in a single autoregulatory cassette," *Proc. Natl. Acad. Sci. USA* 93: 5185–90 (1996).

Huang, M. and J. Summers, "Infection Initiated by the RNA Pregenome of a DNA virus," *Journal of Virology* 65(10): 5435–9 (1991).

Ishizaka et al., "Isolation of Active Ribozymes from an RNA pool of Random Sequences Using an Anchored Substrate RNA," *Biochemical and Biophysical Research Communications* 214(2): 403–9 (1995).

Jayawickreme C.K. and T.A. Kost, "Gene expression systems in the development of high–throughput screens," *Current Opinion in Biotechnology* 8: 629–34 (1997).

Johnson et al., "Identification of Zinc Finger mRNAs Using Domain–Specific Differential display," *Analytical Biochemistry* 236: 34–52 (1996).

Kashani–Sabet, M and K.J. Scanlon, "Application of ribozymes to cancer gene therapy," *Cancer Gene Therapy* 2(3): 213–23 (1995).

Kawasaki et al., "Selection of the best target site for ribozyme–mediated cleavage within a fusion gene for adenovirus E1A–associated 300 kDa protein (p300) and luciferase," *Nucleic Acids Research* 24(14): 3010–6 (1996).

Keck et al., "Role of DNA Replication in Vaccinia Virus Gene Expression: A Naked Template is Required for Transcription of Three Late Trans–Activator Genes," *Cell* 61: 801–9 (1990).

Kijima et al., "Therapeutic Applications of Ribozymes," *Pharmac. Ther.*68: 246–67 (1995).

Kitamura et al., "Efficient screening of retroviral cDNA expression libraries," *Proc. Natl. Acad. Sci. USA* 92: 9146–50 (1995).

Koizimi et al., "Design of RNA enzymes distinguishing a single base mutation in RNA," *Nucleic Acids Research* 17(17): 7059–7071 (1989).

Lieber, A. and M. Strauss, "Selection of Efficient Cleavage Sites in Target RNAs by Using a Ribozyme Expression Library," *Molecular and Cellular Biology* 15(1): 540–51 (1995).

Lieber, A. and M.A. Kay, "Adenovirus–Mediated Expression of Ribozymes in Mice," *Journal of Virology* 70(5): 3153–8 (1996).

Markowitz et al., "A Safe Packaging Line for Gene Transfer: separating Viral Genes on Two Different Plasmids," *Journal of Virology* 62(4): 1120–4 (1988).

Markowitz et al., "Construction and Use of a Safe and Efficient Amphotrophic Packaging Cell Line," *Virology* 167:400–6 (1988).

McCall et al., "Minimal sequence requirements for ribozyme activity," *Proc. Natl. Acad. Sci. USA* 89: 5710–4 (1992).

Miller et al., "Cell–surface receptors for retroviruses and implications for gene transfer," *Proc. Natl. Acad. Sci. USA* 93: 11407–13 (1996).

Miller, D.G. and A.D. Miller, "A Family of Retroviruses That Utilize Related Phosphate Transporters for Cell Entry," *Journal of Virology* 68(12): 8270–6 (1994).

Miller, A.D., "Human gene therapy comes of age," *Nature* 357: 455–60 (1992).

Miller, A.D and G.J. Rosman, "Improved Retroviral Vectors for Gene Transfer," *Biotechniques* 7: 980–90 (1989).

Miller, A.D. and C. Buttimore, "Redesign of Retrovirus Packaging Cell Lines to Avoid Recombination Leading to Helper Virus Production," *Molecular and Cellular Biology* 6(8(: 2895–902 (1986).

Mizuuchi et al., "Cloning and Simplified Purification of *Escherichia coli* DNA Gyrase A and B Proteins," *The Journal of Biological Chemistry* 25914): 9199–201 (1984).

Murphy, F.L. and T.R. Dech, "Alternation of substrate specificity for the endoribonucleotide cleavage of RNA by the Tetrahymena ribozyme," *Proc. Natl. Acad. Sci. USA* 86: 9218–22 (1989).

Muzyczka, N., "Use of Adeno–Associated Virus as a General Transduction Vector for Mammalian Cells," *Current Topics in Microbiology and Immunology* 158: 97–123 (1992).

Peer et al., "Production of high–titer helper–free retroviruses by transient transfection," *Proc. Natl. Acad. Sci. USA* 90: 8392–6 (1993).

Perreault et al., "Relationship between 2'–Hydroxyls and Magnesium Binding in the Hammerhead RNA Domain: A Model for Ribozyme Catalysis," *Biochemisty* 30: 4020–5 (1991).

Perriman et al., "Extended target–site specificity for an hammerhead ribozyme," *Gene* 113: 157–63 (1992).

Peterson, F.C. and C.L. Brooks, "Identification of a Motif Associated with the Latogneic Actionsof Human Growth Hormone," *The Journal of Biological Chemistry* 272(34): 21444–8 (1997).

Rossi, J.J., "Controlled, targeted, intracellular expression of ribozymes: progress and problems," *Trends in Biotechnology* 13: 301–6 (1995).

Ruffner et al., "Sequence Requirements of the Hammerhead RNA Self–Cleavage Reaction," *Biochemistry* 29: 10695–702 (1990).

Sambrook, Fritsch, and Maniatis (Eds.) *Molecular Cloning: A Laboratory Manual* 2nd ed. New York: Cold Spring Harbor Laboratory Press, 1989 pp. 7.6–7.29 and 7.37–7.57.

Samulski et al., "Helper–Free Stocks of Recombinant Adeno–Associated Viruses: Normal Integration Does Not Require Viral Gene Expression," *Journal of Virology* 63(9): 3822–8 (1989).

Schultze–Merker et al., "The protein product of the zebrafish homologue of the mouse T gene is expressed in nuclei of the germ ring and the notochord of the early embryo," *Development* 116(4): 1021–33 (1992).

Sczakiel, G., "The Design of Antisense RNA," *Antisense & Nucleic Acid Drug Development* 7: 439–44 (1997).

Shore et al., "Ribozyme–mediated cleavage of the BCRABL oncogene transcript: in vitro cleavage of RNA and in vivo loss of P210 protein–kinase activity," *Oncogene* 8: 3183–8 (1993).

Sigurdsson, S.T. and F. Eckstein, "Structure–function relationships of hammerhead ribozymes: form understanding to application," *Trends in Biotechnology* 13: 286–9 (1995).

Soares, M.B., "Identification and cloning of differentially expressed genes," *Current Opinion in Biotechnology* 8: 542–6 (1997).

Stoker, A.W., Chapter 6 "Retroviral vectors," of *Molecular Virology: A Practical Approach* Davidson, A.J. and R.M. Elliott (Eds.) Oxford: IRL Press, 1993 pp. 171–197.

Stone, B. and W. Wharton, "Targeted RNA fingerprinting: the cloning of differentially–expressed cDNA fragments enriched for members of the zinc finger gene family," *Nucleic Acids Research* 22(13): 2612–8 (1994).

Straus, D.B. and A. Weiss, "Genetic Evidence for the Involvement of the ICK Tyrosine Kinase in Signal Transduction through the T Cell Antigen Receptor," *Cell* 70: 585–93 (1992).

Sullenger, B.A., "Colocalizing Ribozymes with Substrate RNAs to Increase Their Efficacy as Gene Inhibitors," *Applied Biochemistry and Biotechnology* 54: 57–61 (1995).

Sullenger et al., "Expression of Chimeric tRNA–Driven Antisense Transcripts Renders NIH 3T3 Cells Highly Resistant to Moloney Murine Leukemia Virus Replication," *Molecular and Cellular Biology* 10(12): 6512–23 (1990).

Sullenger, B.A. and T.R. Cech, "Tethering Ribozymes to a Retroviral Packaging Signal for Destruction of Viral RNA," *Science* 262: 1566–9 (1993).

Sun et al., "Anti–HIV Ribozymes," *Molecular Biotechnology* 7: 241–51 (1997).

Sun et al., "Resistance to human immunodeficiency virus type 1 infection conferred by transduction of human peripheral blood lymphocytes with ribozyme, antisense, or polymeric trans–activation response elements constructs," *Proc. Natl. Acad. Sci. USA* 92: 7272–6 (1995).

Uhlenbeck, O.C., "A small catalytic oligoribonucleotide," *Nature* 328: 596–603 (1987).

Von Stein et al., "A high throughput screening for rarely transcribed differentially expressed genes," *Nucleic Acids Research* 25(13): 2998–602 (1997).

Weiss et al., "Signal transduction by the T cell antigen receptor," *Seminars in Immunology* 3: 313–24 (1991).

Wyatt et al., "Replication–Deficient Vaccinia Virus Encoding Bacteriophage T7 RNA Polymerase for Transient Gene Expression in Mammalian Cells," *Virology* 210: 202–5 (1995).

Xie et al., "A ribozyme–mediated, gene "knockdown" strategy for the identification of gene functionin zebrafish," *Proc. Natl. Acad. Sci. USA* 94: 13777–81 (1997).

Xiong et al., "Sindbis Virus: An Efficient, Broad Host Range Vector for Gene Expression in Animal Cells," *Science* 243: 1188–91 (1989).

Zhao et al., "Generating loss–of–function phenotypes of the *fushi tarazu* gene with a targeted ribozyme in Drosophila," *Nature* 365: 448–51 (1993).

Zhou et al., "Inhibition of HIV–1 in human T–lymphocytes by retrovirally transduced anti–tat and rev hammerhead ribozymes," *Gene* 149: 33–9 (1994).

* cited by examiner

Figure 1

```
5'-N NNN NNN UGU/C NUN NNN UGU/C -3'
 3'- N  ACA/G NA    NNN ACA/G -5'
         A   C
         A    U   A
         G     G
         C    A   G
         A     A
         G    C   G
         G    C   U
           A     G
            G  U
```

Figure 2

1) 5'-CCAGCTC C TGA TGA GTC CGT GAG GAC GAA ACCAGGA-3'
2) 5'-GGCCGTT C TGA TGA GTC CGT GAG GAC GAA ACGTCGC-3'
3) 5'-CTCGCCG C TGA TGA GTC CGT GAG GAC GAA ACACGCT-3'
4) 5'-GCAGATG C TGA TGA GTC CGT GAG GAC GAA ACTTCAG-3'
5) 5'-TGGTCAC C TGA TGA GTC CGT GAG GAC GAA AGGGTGG-3'
6) 5'-AGCGGCT C TGA TGA GTC CGT GAG GAC GAA AAGCACT-3'
7) 5'-CATGGCG C TGA TGA GTC CGT GAG GAC GAA ACTTGAA-3'
8) 5'-GCTCCTG C TGA TGA GTC CGT GAG GAC GAA ACGTAGC-3'
9) 5'-CGTCCTT C TGA TGA GTC CGT GAG GAC GAA AAGAAGA-3'
10) 5'-CGCCCTC C TGA TGA GTC CGT GAG GAC GAA AACTTCA-3'
11) 5'-TGCGGTT C TGA TGA GTC CGT GAG GAC GAA ACCAGGG-3'
12) 5'-CCTCCTT C TGA TGA GTC CGT GAG GAC GAA AAGTCGA-3'
13) 5'-GTAGTTG C TGA TGA GTC CGT GAG GAC GAA ACTCCAG-3'
14) 5'-TGATATA C TGA TGA GTC CGT GAG GAC GAA ACGTTGT-3'
15) 5'-GGATCTT C TGA TGA GTC CGT GAG GAC GAA AAGTTCA-3'
16) 5'-GGTCGGC C TGA TGA GTC CGT GAG GAC GAA AGCTGCA-3'
17) 5'-GCAGCAG C TGA TGA GTC CGT GAG GAC GAA ACGGGGC-3'
18) 5'-CAGGGCG C TGA TGA GTC CGT GAG GAC GAA ACTGGGT-3'
19) 5'-CCAGCAG C TGA TGA GTC CGT GAG GAC GAA ACCATGT-3'
20) 5'-CCATGCC C TGA TGA GTC CGT GAG GAC GAA AGAGTGA-3'

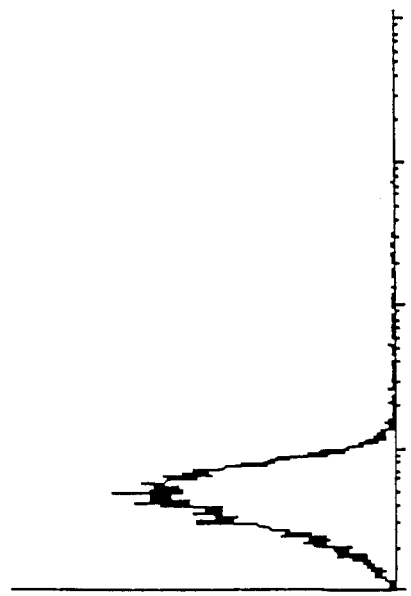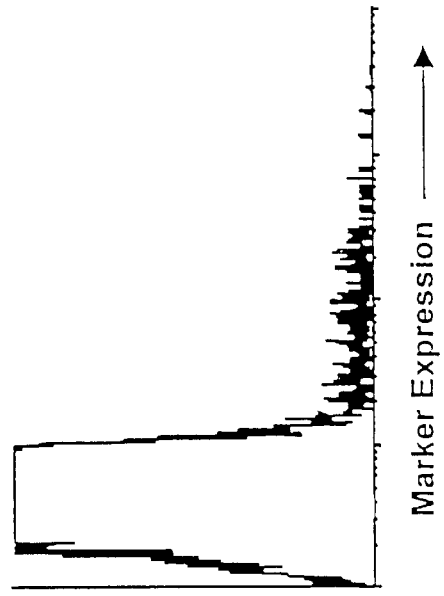

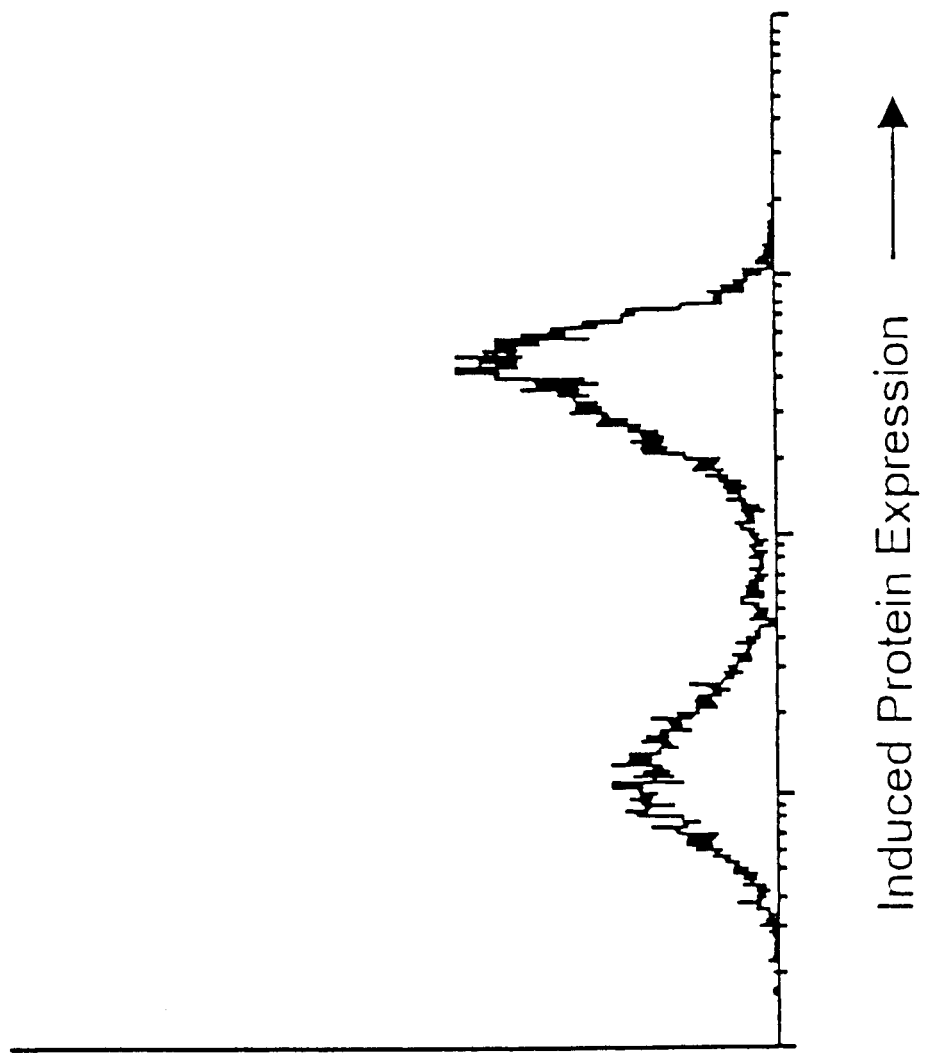

USE OF RIBOZYMES FOR FUNCTIONATING GENES

This application is a 371 PCT/US99/03166 Feb. 12, 1999 which is a CIP of Ser. No. 09/023,992 Feb. 13, 1998 now abandoned.

INTRODUCTION

1. Technical Field

The present invention is related to methods and compositions for identifying a gene or genes associated with the generation of a specific cellular phenotype or a specific cellular response using combinatorial libraries of catalytic RNA directed against RNA sequences encoding structural or functional polypeptide motifs. The invention is exemplified by use of a combinatorial ribozyme library to target sequences in mRNAs encoding zinc finger, protein kinase and integrin motifs.

2. Background

Properly functioning cells are necessary for any organism, including humans, to thrive; improperly functioning cells may contribute to the development of pathogenic or disease states in a given individual, including generation of cancers, autoimmune diseases, innate immunodeficiencies, neurologic diseases, and inborn errors of metabolism. In addition, even properly functioning cells may contribute to pathogenic states, including susceptibility to infectious agents, atopic/allergic pathogeneses, and pathogenic states associated with allograft transplantation. In both of the above cases, inappropriate expression, regulation, or function of a specific gene product or gene products within a cell may lead to the improper behavior of that cell within the context of its normal function in an organism. Often, the activity of a single gene product, such as a protein or polypeptide, will affect the expression, regulation, or function of other gene products within the same cell or within neighboring cells. Aberrant expression, regulation, or function of these aggregated gene products may then result in the development of specific disease phenotypes or syndromes.

Approaches that have been used to identify genes which are potentially involved in a disease development process include identification of genes which are mutated in certain diseases and differential display of actively expressed transcripts in normal versus pathologic cells. These approaches have given rise to a rapid increase in the number of DNA sequences associated with various pathologic states. These sequences include not only full length genes, but also cDNA sequences comprised of partial gene sequences or ESTs. Although sequences identified by these processes are associated with a pathologic state, it is difficult to ascertain a priori whether a given gene is directly involved in the disease development process, or whether its expression occurs in a secondary fashion after the pathogenic process has already begun.

Involvement of particular genes as causative agents in the disease development process can be confirmed by a number of methods. Confirmation of the role of particular genes in the disease development process using partial cDNA sequences is more difficult to assess, however, because many of the methods used require knowledge of the full gene sequence. Thus, while the number of potentially novel genes has expanded exponentially, identification of the functions ascribed to most of these genes and gene sequences, as well as their prospective roles in disease development has lagged far behind.

One way to establish the causative effect of a gene or gene sequence in the development of a specific cellular phenotype or response is to interfere with the expression or function of that gene or gene product, and then to determine the resulting effect on that cellular phenotype or response. Methods utilized to interfere with gene expression in vivo involve gene targeting by homologous recombination in embryonic stem cells, re-implantation of the stem cells, gestation of the embryos, and isolation of animals bearing diallellic deletions in the gene of interest, so called "transgenic technology". The development of transgenic technology has been an important advance in the tools available for studying the function of genes at the organismal level. Because this procedure can take up to a year to complete, however, it is not an efficient process for the high-throughput evaluation of genes or gene products as causative agents and as potential therapeutic targets. Methods utilized to interfere with gene expression in vitro include gene deletion or inactivation by homologous recombination or triplex technology, RNA transcript inactivation or cleavage by antisense or ribozyme technology, and protein inactivation or down-regulation by antipeptide antibody fragments or expression of randomized peptides. A limitation to utilizing systems expressing randomized peptides, antisense RNA molecules, or anti-peptide antibodies to identify gene functions and/or signaling pathways in cells is that these compounds do not act catalytically as is the case for ribozymes and therefore, relatively high intracellular concentrations may be necessary to affect a cellular function or phenotype.

Ribozymes are RNA molecules that act as enzymes and can be engineered to cleave other RNA molecules. Thus, ribozymes perform functions in the cell that are very different from ordinary RNA, in that, after binding selectively to their specific mRNA target, they act catalytically to cut, or cleave, target RNA molecules at specific sites. If an mRNA target in a cell is destroyed, the particular protein for which that mRNA molecule carries information is not produced. The ribozyme itself is not consumed in this process, and can act catalytically to cleave multiple copies of mRNA target molecules. One way to use ribozymes to identify the function of novel gene sequences is to introduce a pool of ribozymes with degenerate target recognition sites into cells in order to reduce or eliminate the expression of a gene or gene product involved in the generation of a specific cellular phenotype or response. In this strategy, ribozymes bearing the appropriate recognition sequences eliminate or reduce expression of the target gene, while ribozymes not bearing the appropriate recognition sequences do not. Loss of a specific cellular phenotype or response associated with elimination or reduction in expression of a target gene indicates involvement of that particular gene in the development of that particular phenotype or response.

Of the estimated 100,000 expressed genes in a mammalian cell, approximately one-third are likely to be necessary for normal cell respiration, metabolism, or viability. A totally degenerate ribozyme library would by necessity include ribozymes directed against these "housekeeping genes" as well as against genes involved in disease processes. Cleavage of housekeeping RNAs results in compromised cellular viability, so no information can be gained from a great number of the ribozyme sequences in such a library. This problem reduces the efficiency of using totally degenerate ribozyme libraries to identify and assign a function to novel genes or gene sequences with respect to a disease development process. Another major limitation to this system is the need to synthesize and express a completely randomized library of nucleic acids and to screen the library for functional activity. The minimal targeting or recognition sequence of a ribozyme is generally 12 nucleotides and a totally random library would contain $4^{12}$ or approximately 16 million ribozymes. Due to the large number of permutations of the ribozyme binding sequences, a specific targeting approach is essential. It is therefore of interest to develop a high throughput ribozyme based screening system that limits the potential target sequences for evaluation to those which have an increased probability of being associated with a molecular pathway that is related to a disease or phenotype.

Relevant Literature

An RNA molecule not naturally occurring in nature having enzymatic activity independent of any protein is disclosed in U.S. Pat. No. 4,987,071 General rules for the design of hammerhead ribozymes that cleave target RNA in trans are described in Haseloff and Gerlach, (1988) *Nature* 334:585–591. Miniribozymes are disclosed in Uhlenbeck, (1987) *Nature* 328:596–603. Methods for optimizing cleavage of a target RNA by a ribozyme are described in U.S. Pat. No. 5,496,698. Reporter gene suppression by engineered hammerhead ribozymes in mammalian cells is described in Cameron and Jennings, (1989) *Proc. Natl. Acad. Sci.* (USA) 86:9139–9143. Ribozyme expression from a retroviral vector is described in Sullenger and Cech, (1993) *Science* 262:1566–1569. The expression of hammerhead ribozymes operatively linked to a T7 promoter is described in Chowrira et al., (1994) *J. Biol. Chem.* 269:25856–25864. Co-localizing ribozymes with substrate RNAs to increase their efficacy as gene inhibitors is described in Sullenger, (1995) *Appl. Biochem. Biotechnol.* 54:57–61. Screening of retroviral cDNA expression libraries is described in Kitamura, et al., (1995) *Proc. Nat. Acad. Sci.* (*USA*) 92:9146. Selection of efficient cleavage sites in target RNAs by using a ribozyme expression library is described in Lieber and Strauss, (1996) *Mol. Cell. Biol.* 15:540–551. Approaches for the identification and cloning of differentially expressed genes is discussed in Soares, (1997) *Curr. Opin. Biotechnol.* 8:542–546. The development of high-throughput screen is discussed in Jayawickreme and Kost, (1997) *Curr. Opin. Biotechnol.* 8:629–634. The high throughput screen for rarely transcribed differentially expressed genes is described in von Stein et al., (1997) *Nucleic Acids Res.* 25:2598–2602. High-throughput genotyping is disclosed in Hall, et al., (1996) *Genome Res* 6:781–790. Methods for screening transdominant intracellular effector peptides and RNA molecules are disclosed in WO97/27212 and WO97/27213.

SUMMARY OF THE INVENTION

Methods and compositions for their use therein, are provided for determining and validating a link between a target nucleic acid which includes a nucleotide sequence that encodes a motif of interest and and a diseases and/or phenotype using a combinatorial ribozyme library. Ribonucleotide members of the ribozyme library include a binding region which is complementary to a transcription product of the target nucleic acid and a catalytic domain which cleaves a sequence within a transcription product of the target nucleic acid coding for the motif of interest so that expression of the transcription product is disrupted. The method includes the steps of designing a combinatorial ribozyme library by analyzing a consensus nucleotide sequence encoding a protein motif and synthesizing embers of a library of sense strands of DNA which, when expressed as RNA constitute the members of a ribozyme library; annealing the sense strands to antisense strands to form double stranded DNAs, introducing the double stranded DNAs, which optionally include a means for determining directionality of expression, into expression vectors; contacting a host cell culture containing one or more host cells with the expression vector(s) under conditions such that the expression vectors transfect or infect the host cells; growing the host cells to express the ribozyme(s); analyzing the phenotype of, or a suitable detectable marker in, the resultant transfected or infected host cells to identify any altered host cell by virtue of an alteration in phenotype or marker as compared to unmodified host cells; isolating altered host cells; and correlating the phenotype of altered host cells with the identity of the target nucleic acid encoding the motif of interest by isolating DNA from the isolated altered host cells and determining the specific ribozyme sequence contained in the isolated DNA which is complementary to sequences in the target nucleic acid so as to assign a function to the product coded for by the target nucleic acid. The ribozyme libraries and subject methods can be used, for example, for functionating a gene encoding a protein that contains a motif of interest, such as a gene involved in apoptosis, drug susceptibility, cell cycle regulation, cell differentiation or transformation of a host cell.

BRIEF DESCRIPTION OF THE DRAWINGS

FIG. 1 shows the general structure of the members of a combinatorial ribozyme library annealed to an mRNA encoding the minimal recognition sequence of the reverse translated zinc finger motif (SEQ ID NO:43), C-X-X-C (X=any amino acid). Upper strand (SEQ ID NO:1) is the targeted mRNA with the ribozyme cleavage site indicated. The lower stand (SEQ ID NO:2) is a hammerhead ribozyme annealed to the mRNA target. (N=any nucleotide).

FIG. 2 shows the nucleotide sequence of oligonucleotides encoding an anti-EGFP hammerhead ribozyme (SEQ ID NOS:3–22).

BRIEF DESCRIPTION OF PREFERRED EMBODIMENT(S)

Figure 3C:
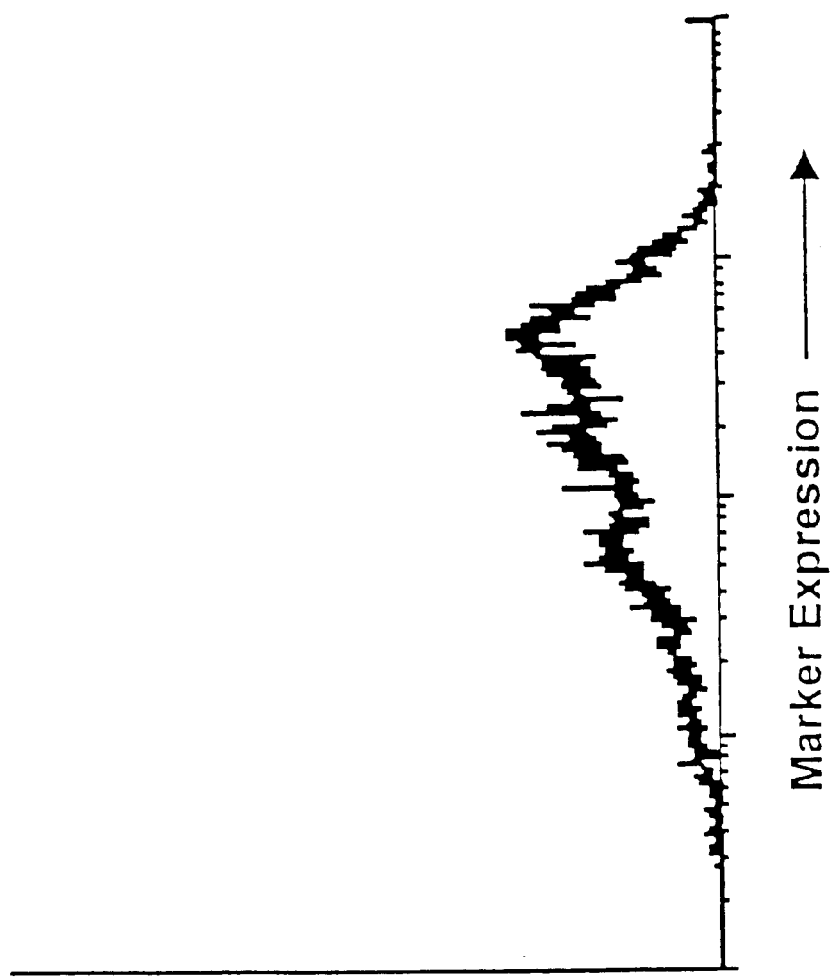
FIG. 3 demonstrates the isolation of cells expressing a selectable marker associated with a ribozyme-expressing construct from Jurkat T-cell cultures transduced with a library of ribozymes. The selectable marker is the cell surface molecule Lyt-2 (CD8a). Cells expressing the Lyt-2 marker are isolated from the rest of the population using a fluorescence activated cell sorter. The X axis depicts marker expression. The Y axis depicts cell number. The histogram in FIG. 3A shows the profile of marker expression in transduced cultures. The histogram in FIG. 3B shows the same histogram with an expanded Y axis to reveal the marker positive population shifting rightward in the histogram. Marker positive cells isolated by flow cytometric cell sorting were grown in culture, and marker expression was re-analyzed in the enriched cultures. The histogram in FIG. 3C shows results from this re-analysis. All cells in the enriched cultures express the marker, demonstrating the ability to isolate a stable population of cells expressing a library of pooled ribozymes using this method.

In the present invention, a combinatorial ribozyme library designed for a target nucleic acid, DNA or RNA, that contains a nucleotide sequence encoding a motif of interest is developed and used as a means of assigning a function to the target nucleic acid. The term "ribozyme" is intended to mean a synthetic RNA molecule that acts as an enzyme and has been engineered to cleave other RNA molecules; after binding selectively to a specific RNA target molecule, it acts catalytically to cut, or cleave, a specific RNA target molecule in a region encoding a motif such as a zinc finger, a protein kinase or an integrin. Ribonucleotide members of the ribozyme library include a binding region which is complementary to a transcription product of the target nucleic acid and a catalytic domain which cleaves a sequence within a transcription product of the target nucleic acid coding for the motif of interest so that expression of the transcription product is disrupted. The binding region generally flanks the catalytic domain. The ribozyme library is introduced into a viral vector such as a retrovirus vector or a plasmid vector which is then used to infect or transfect a host cell culture that is grown to express the ribozyme library; depending upon the system used, the vector can be incorporated into the host cell genome or can be episomal. Optionally, the DNA of the vector is supercoiled. The host cell culture includes at least one host cell and can contain a plurality of host cells. The host cell generally is a mammilian cell but can be a lower or higher plant cell, an invertebrate cell or a bacterial cell. The expression of the ribozyme in the host cell alters the phenotype of the host cell so that a function for the product encoded by the target nucleic acid can be assigned based upon the change in phenotype. The term "function" is intended to mean a detectable or measurable event. The target nucleic acid encodes an expression product that is directly or indirectly involved in a measurable function or phenotype in a host cell containing the target nucleic acid. Generally the expression product is a protein, including signaling molecules and structural proteins. The term "motif" intended to mean a conserved or partially conserved sequence shared by a functionally or structurally related class or family of proteins. The term "phenotype" is intended to mean a characteristic of a specific cell or cell population and includes physical functions such as membrane permeability, physiological functions which include those affected directly or indirectly by regulatory effectors, and biochemical and biological characteristics and functions such as protein synthesis and enzyme activity. The host cell exhibiting an altered phenotype is identified using and isolated using any of a variety of standard techniques. DNA coding for the ribozyme is identified in the DNA isolated from the host cell, conveniently by PCR amplification of the mRNA or genomic DNA coding for the ribozyme using a primer pair derived from vector sequences flanking the ribozyme insert. The PCR product is then sequenced to obtain the sequence of the ribozyme-coding sequence, which not only identifies the biologically active ribozyme, but also the identity of the target nucleic acid.

There are several advantages to the subject invention. By targeting the combinatorial ribozyme library to conserved or partially conserved motifs associated with known functions or properties of proteins or polypeptides containing such motifs, the number of ribozymes that need to be constructed and analyzed is significantly reduced (less than about 100,000) in comparison to a random library (over 16 million). The ability to eliminate the step of amplifying plasmid DNA in bacteria such as *E. coli* is a major cost saving advantage as well as a time saving advantage over existing technologies: removal of the *E. coli* amplification can subtract several labor intensive days from the entire process. Furthermore, the subject process lends itself to automation when implemented in a matrix format or a 96-well or similar multi-well format. The simultaneous construction, delivery and expression of multiple members of a combinatorial ribozyme library and their analysis offers the advantage that a large number of ribozymes can be expressed conveniently in host cell cultures, thereby enabling the identification of genes and determining the function of genes by a manageable high throughput screening process in a relatively short period of time. Furthermore, the combinatorial ribozyme library can be constructed with synthetic oligonucleotide DNA which offers the additional advantage that directionality is conveniently achieved by incorporating unique restriction enzyme sites at both ends of each of the oligonucleotides used to prepare the double-stranded DNA coding for these molecules so that double-stranded DNA is ligated to the delivery vector in the correct orientation for expression. This overcomes the problem that if the same restriction enzyme site, blunt ends or restriction enzyme sites comprising compatible cohesive ends are used for the ligation, theoretically about 50% of all the constructs would be ligated in the incorrect orientation. Other advantages of the subject invention include the capability to regulate the magnitude and timing of nucleic acid expression and high throughput delivery. Operatively linking the oligonucleotide DNAs encoding the combinatorial ribozyme library to a regulatable promoter provides temporal and/or cell type specific control throughout the screening assay. Additionally, the magnitude of ribozyme expression can be modulated using promoters that differ in their transcriptional activity.

Ribozyme technology in particular offers several advantages over other methods used to determine which genes are relevant to a disease because as used in the subject invention they are selective for a specific target motif sequence and act catalytically, rather than in a stoichiometric manner. Thus, a single ribozyme molecule can cleave and inactivate up to 100 RNA transcripts, while a single antisense or antipeptide molecule will only inactivate one RNA transcript or one polypeptide. These properties can be used to identify the role of a target genetic sequence and to characterize its cellular function and the function of its encoded product. In the disclosed invention, it is not necessary to develop conformational models of the target nucleic acids to identify regions which are particularly accessible. Such models typically are developed using computer-assisted predictions of possible thermodynamically stable secondary structures. The need for such computer generated models is avoided by creating a combinatorial ribozyme library targeted to nucleic acids encoding a motif of interest. Additionally, sustained expression of ribozyme activity can be achieved by utilizing plasmid or viral based expression constructs driven by cellular promoters in order to constitutively express high levels of ribozymes directed against the target of interest, ensuring sufficient levels of cellular genes are inactivated to cause a detectable change in cellular phenotype or response.

Another advantage to using ribozyme molecules for inactivation of cellular RNA transcripts is that recognition of an mRNA target by the ribozyme molecule requires the complementary base-pairing of only 12–14 nucleotides. Knowledge of the entire sequence of the gene of interest is therefore not necessary. This characteristic, together with the aforementioned ability of ribozymes to function catalytically makes them useful for identifying the roles of genes where only partial sequences are known, as well as the roles of genes where the full length sequence is known.

By constructing combinatorial ribozyme libraries bearing recognition sites derived from DNA or RNA sequences encoding known protein functional motifs, the likelihood that a ribozyme in the library will cleave a transcript involved in a "functional" gene is greatly increased. An additional advantage to this strategy is that more than one combinatorial library can be introduced into host cells simultaneously, allowing isolation of genes containing combinations of specific motifs, which contributes to specificity of the ribozyme for a particular gene. For example, one can isolate with equal ease "genes which are transmembrane protein receptors with intracellular tyrosine kinase domains and SH2 regions" as well as "all genes with kinase function."

The combinatorial ribozyme library is designed by analyzing a consensus nucleotide sequence coding for a protein motif of interest. Motifs of interest are identified by use of scientific literature; public and/or private databases; and other sources (e.g., Prosite: http://expasy/hcuge.ch/) that contain information regarding the relatedness of various proteins based on amino acid sequence homology. Proteins with one or more shared function or class tend to contain similar amino acid patterns or motifs that are common for each class of protein. For example receptor tyrosine kinases, enzymes involved in the transfer of phosphate to tyrosine residues on protein substrates, often contain the amino acid sequence: G-X-H-X-N-[LIVM]-V-N-L-L-G-A-C-T (SEQ ID NO:23) wherein X=any amino acid, and [ ]=containing only one of the amino acids listed within the brackets. Examples of tyrosine kinases that contain this sequence are platelet-derived growth factor, macrophage colony stimulating factor receptor (fns oncogene), stem cell factor receptor (kit oncogene), and vascular endothelial growth factor (VEGF) receptors Flt-1 and Flk-1/KDR. These molecules have been demonstrated to participate in various signal transduction pathways.

The subject invention is designed to identify molecules, previously known or unknown, to have comparable roles in the function of a host cell(s) and to be specifically associated with disease states or phenotypes. Other examples of conserved motifs that are contained in functionally related classes of proteins that are critical for cell function are proteases. For instance, caspase-1, known as interleukin-1 beta converting enzyme (ICE), represents a family of proteases (caspase-1 to 12) involved in apoptosis which has the consensus motifs K-P-K-[LIVMF](4)-Q-A-C-[RQG]-G (SEQ ID NO:24) and H-X(2,4)-[SC]-X(4)-[LIVMF](2)-[ST]-H-G (SEQ ID NO:25). For abbreviations, see supra. *Caenorhabditis elegans*, ced-3, and Drosophila ICE also contain these motifs.

Other motifs are shared by proteins that have a common structural relationship. For example, the zinc finger motif has been found in a variety of DNA-binding proteins. One zinc finger is known as the C3HC4 domain and has the consensus sequence: C-X-H-X-[LIVMFY]-C-X(2)-C-[LIVMYA] (SEQ ID NO:26). This motif is found in a diverse range of proteins including the BRCA1 protein that is associated with breast cancer, protein RAG-1 that is involved in rearrangement of immunoglobulin and T-cell receptor genes and in RO/SS-A which is associated with lupus and Sjögren's syndrome. Another example is a portion of the integrin family that has the conserved sequence: G-X-[GNQ]-X(1,3)-G-X-C-X-C-X(2)-C-X-C (SEQ ID NO:27). The integrins are involved in cell to cell and cell to matrix adhesion: cellular functions that may be important in metastasis and tumor invasion.

Motifs found in protein kinases, integrins, caspases and zinc-finger domains have been described. The combinatorial ribozyme library, however, can be designed to target the mRNA encoding any protein for which a conserved sequence can be identified. These include enzymes such as proteases, structural proteins and signaling molecules.

Different regions within the same motif can be targeted. In addition, if a family or class of proteins contains more than one motif, multiple motifs also can be targeted. The targeted motifs are not limited to those found in proteins with known mammalian regulatory functions but also can be motifs that have only been identified in other organisms such as yeast, Drosophila, *Caenorhabditis elegans*. Therefore, human genes critical to disease processes or phenotypes that encode proteins containing motifs similar to those in genes in lower eukaryotes can be identified.

In general, motifs that are derived from highly conserved sequences, are not desirable in making a combinatorial ribozyme library, as the sequence would be present in every potential target. By highly conserved is meant that all amino acids found in a contiguous sequence of amino acids found in a motif are identical. An optimal situation is where several conserved sequence possibilities exist, all of which can contribute to a conserved motif. By conserved is meant that amino acid sequences in a motif are at least 80% and more preferred at least 90% identical. This increases the target specificity of the combinatorial ribozyme pool. In this case, individual ribozymes contained within the library specifically target the production of functionally unique molecules. Ribozymes can be designed to motifs of any length. As the length of a motif increases, different ribozymes can be targeted to nucleotides encoding contiguous conserved or partially conserved amino acid sequences throughout the length of the motif. Generally, a combinatorial ribozyme library is designed to target an RNA encoding a partially conserved amino acid sequence found in a motif of interest. By partially conserved is meant that the amino acid sequences found in a motif are at least 60% identical.

When designing the combinatorial ribozyme library, all combinations of nucleotide sequences that give rise to the chosen motif based on codon degeneracy and usage and the location of the ribozyme cleavage sites are taken into consideration. The target-binding nucleotides of the combinatorial ribozyme library are therefor degenerate. This insures that the ribozyme library can target all possible permutations of the targeted sequence. For expression, both sense and antisense sequences are prepared: the sense strands are annealed to the corresponding antisense strands to form double stranded DNA molecules. When transcribed in a host cell culture, the sense DNA produces RNA which is complementary to an mRNA sequence encoding a motif of interest and contains a catalytic domain designed to leave the mRNA sequence. Each member of a ribozyme library includes two stretches of antisense oligonucleotides, each preferably between 5–9 nucleotides (nt) long and optimally 6 to 8 nucleotides long, to bind to the mRNA, with the sequence forming the catalytic domain or catalytic core in between. The bases immediately adjacent to either side of the catalytic core in the sense strands constitute the ribozyme binding sequence when expressed as RNA that is complementary to a mRNA sequence. The mRNA target contains a consensus cleavage site for the ribozyme. For hammerhead ribozymes the triplet GUC is best but the sequence NUN (N=any nucleotide) also can be targeted. If the catalytic domain is derived from a hairpin ribozyme, the triplet GUC is also preferred (Kashani-Sabet and Scanlon, (1995) *Cancer Gene Therapy* 2:213–223; Perriman, et al., (1992) *Gene* (*Amst.*) 113:157–163; Ruffner, et al., (1990) *Biochemistry* 29:10695–10702); Birikh, et al., (1997) *Eur. J. Biochem.* 245:1–16; Perrealt, et al., (1991) *Biochemistry* 30:4020–4025). Generally, the entire ribozyme-mRNA binding sequence is about 10 to 30 nucleotides in length with 11–17 nucleotides being preferred. The catalytic region generally is about 22 nucleotides in length. The catalytic region of miniribozymes is generally about 16 nucleotides in length (Uhlenbeck et al. *Nature* 328:596–603).

The oligonucleotides for the sense and antisense DNA strands can be simultaneously synthesized on solid supports in a matrix format, and simultaneously deprotected and cleaved. If complementary pairs of oligonucleotides are simultaneously synthesized, deprotected and cleaved in a matrix format, they can be simultaneously annealed and ligated to a vector. Another method of producing these constructs is to make shorter oligonucleotides with shorter complementary regions. Each partially complementary oligonucleotide, each having one part out of the two parts of the targeted motif and a restriction enzyme site, is annealed, extended using a DNA polymerase, and digested with the appropriate restriction enzymes prior to ligation. For example, when targeting a zinc-finger motif, Cysteine-X-X-Cysteine, where X is any other amino acid, the targeted sequence on the mRNA is 5'-NUGYNNNNNNUGY-3' (SEQ ID NO:28) where N is any base and Y is U or C (see Example 1). The ribozyme pool would need to contain the target sequence 5'-RCANNNNNRCA (SEQ ID NO:29) (R=A or G) in the target binding region. An example is as follows (SEQ ID NO:30–31) (Y=C or T):

5'    GGAAITC<u>RCANNN</u>CTGATGAGTCCGTGA-
      GACTCAGGCACTCCTGCTT<u>TNYGT</u>NCCTAGG5'

Bold indicates the nucleotides encoding the ribozyme catalytic domain and the underlined sequences encode the sites that bind to the complementary mRNA encoding the zinc-finger motif. After annealing, both strands of the oligonucleotide are extended using a DNA polymerase and then restriction enzyme digested, in this example, with EcoR I and BamH I (italicized bases in upper and lower strands, respectively). The length of the complementary region can be longer or shorter depending on the annealing conditions. Extra bases can be added at the 5' ends of both strands to improve cutting by the restriction enzymes. Alternatively, a single oligonucleotide is annealed to the delivery vector, ligated and the complementary strand can be filled in by a DNA polymerase or the complementary strand can be filled in before ligation. Three oligonucleotides can be annealed together with the delivery vector; intervening gaps are filled in by a DNA polymerase and ligated with a DNA ligase.

For annealing the complementary oligonucleotide DNA strands encoding the combinatorial ribozyme library, special conditions are not required. For example, both strands can be dissolved in water then mixed at about a one to one molar ratio. They can be mixed in almost any buffer system, T4 ligase buffer, Exonuclease 3 buffer, Mung Bean Nuclease buffer. No special heating is required, room temperature is adequate. This mixing and annealing of the oligonucleotide strands generally occurs in multiwell microtiter dishes although other appropriate apparatus also can be used. A means for determining directionality of expression can be included in the oligonucleotide DNA. Conveniently the means is the use of unique non-blunt end forming restriction enzyme sites at both ends of the oligonucleotide DNA, so that the two oligonucleotides to be annealed share complementary sequences except at the ends where they will be able to bind to a restriction enzyme site. For the restriction enzyme sites, any non-blunt end forming restriction enzyme site can be used at either end, depending on the sites within the DNA vector into which the oligonucleotide DNA fragment is to be ligated. Having different sites at each end provides directionality for ligation. Any restriction enzyme that produces unique non-blunt cohesive ends suitable for ligation by DNA ligase can be used, for example Aat II, EcoR I, BamH I, Hind III, Pst I. If necessary, a restriction enzyme site with a cohesive end can be used with a restriction enzyme site that produces a blunt end. Alternatively, the two oligonucleotides can be completely complementary, including the ends and digested with restriction enzymes prior to ligation with the delivery vector. In this case, it is preferred that the restriction enzyme sites do not occur within the oligonucleotide DNA encoding the ribozyme, otherwise partial digestions will be required. Restriction enzyme digestion is routinely performed using commercially available reagents according to the manufacturer's recommendations and will vary according to the restriction enzymes chosen.

The members of the combinatorial ribozyme library are introduced into any of a variety of vectors, depending on the availability of restriction enzyme sites, intracellular location, and transcriptional regulatory elements for delivery and expression of the ribozymes in the target host cell. The delivery vector into which the ribozymes are to be ligated is digested with the appropriate restriction enzymes, either simultaneously or sequentially, to produce the appropriate ends for directional cloning of the oligonucleotides. The oligonucleotide DNAs preferably contain compatible ends to facilitate ligation to the vector in the correct orientation. For synthetic oligonucleotide ligation, the ends compatible with the vector can be designed into the oligonucleotides. Alternatively, the compatible ends can be formed by restriction enzyme digestion or the ligation of linkers to the oligonucleotides containing the appropriate restriction enzyme sites. The vector also can be modified by the use of linkers. The restriction enzyme sites are chosen so that transcription of the cloned oligonucleotides from the vector produces a ribozyme targeted to the mRNA transcribed from a target nucleic acid that encodes a motif of interest.

The vector encoding the ribozyme or ribozyme library also may encode a marker protein. The marker protein is used for selection of cells that have been transfected/infected with the library-encoding vector. The marker may provide antibiotic resistance. The marker also may provide for visual selection (for example β-galactosidase or green fluorescent protein). The marker can also be a transmembrane protein (for example CD4).

Once digested, the vector and oligonucleotides can be purified by gel electrophoresis, chromatography or phenol/chloroform extraction and ethanol precipitation. The optimal purification method depends on the size and type of the vector and oligonucleotides, however, both can be used without purification. Generally, the oligonucleotide DNA does not contain 5'-phosphate groups and, therefore, the phosphate groups on the vector produced by restriction enzyme digestion are necessary for oligonucleotide-vector ligation. The 5'-phosphate groups can be added to the oligonucleotides by chemical or enzymatic means before or after annealing and the 5'-phosphate can be removed from the digested vector to prevent vector-vector ligation. For ligation, ratios of oligonucleotide DNA to vector DNA range from approximately 4:1 to 6:1. The ligation reaction is performed using T4 DNA ligase or any other enzyme that catalyzes double stranded DNA ligation. Reaction times and temperature can vary from 5 minutes to 18 hours to from room temperature to 15° C. The delivery vector containing the combinatorial ribozyme library optionally is treated to increase the supercoiling of the delivery vector DNA, for example using DNA gyrase so as to improve uptake of the DNA into a recipient cell, such as a packaging cell or the intended target host cell.

One method for expression of the ribozyme library employs recombitant retroviruses. These vectors generally include as operatively linked components, retroviral long terminal repeats, packaging sequences and cloning site(s) for insertion of heterologous sequences. Other operatively linked components can include a nonretroviral promoter/enhancer and a selectable marker gene. Examples of retrovirus expression vectors which can be used include DC-T5T (Sullenger et al. 1990. *Mol. Cell Biol.* 10:6512–65230), kat (*Blood.* 1994 83:43–50), BOSC (*Proc. Natl. Acad. Sci.* (*USA*) (1993) 90:8392–8396), pBabe (*Proc. Natl. Acad. Sci.* (*USA*) (1995) 92:9146–9150) and RetroXpress™ (Clontech, Palo Alto, Calif.).

In some instances, it is desirable to increase expression of the ribozyme library utilizing other promoters and/or enhancers in place of the promoter and/or enhancers provided in the expression vector. These promoters in combination with enhancers can be constitutive, tissue specific or regulatable. Any promoter/enhancer system functional in the target host cell can be used. (See for example, *Molecular Virology* pp. 176–177; Hofmann, et al. 1996. *Proc. Natl. Acad. Sci.* (*USA*) 93:5185–5190; Coffin and Varmus, 1996. Retroviruses. Cold Spring Harbor Press, NY; Ausubel et al. 1994. Current Protocols in Molecular Biology. Greene Publishing Associates, Inc. & Wiley and Sons, Inc.). Examples include: CMV immediate-early promoter, SV40 promoter, thymidine kinase promoter, metallothionein promoter, and the tetracycline operator (Hoffmann et al., (1996) *Proc. Natl. Acad. Sci* (*USA*) 93:5185–5190). Other methods to obtain recombinant retrovirus particles also can be used. For example, the oligonucleotide DNAs are functionally linked to eukaryotic transcriptional elements and are flanked by a retroviral packaging signal and 5' and 3' LTRs. This entire retrovirus construct is functionally linked to the T7 RNA polymerase promoter and T7 terminator. Also encoded by the vector but not within the retroviral construct is a gene functionally linked to a eukaryotic promoter that expresses a T7 RNA polymerase (T7pol) that contains a nuclear localization signal (T7pol-nls). Following transfection of this vector into a retroviral packaging cell, the T7-nls is expressed and localized in the nucleus where it transcribes recombinant retroviral genomes that are packaged by the retroviral genes expressed by the packaging cell. Because of the high transcriptional activity of T7pol-nls, high recombinant retrovirus titers can be achieved. Similar vectors, utilizing other DNA-dependent RNA polymerases, such as, SP6 or T3 also can be used.

To package the recombinant retrovirus vectors containing the ribozyme library, cell lines are used that provide in trans the gene functions deleted from the recombinant retrovirus vector such that the vector is replicated and packaged into virus particles. The genes expressed in trans encode viral structural proteins and enzymes for packaging the vector and carrying out essential functions required for the vector's expression following infection of the target host cell. Packaging cell lines and retrovirus vector combinations that minimize homologous recombination between the vector and the genes expressed in trans are preferred to avoid the generation of replication competent retrovirus. Packaging systems that provide essential gene functions in trans from co-transfected expression vectors can be used, as can packaging systems that produce replication competent retroviruses. Following packaging, the recombinant retrovirus is used to infect target cells of interest. The envelope proteins expressed permit infection of the target cell by the recombinant retrovirus particle. Retrovirus packaging cell lines which can be used include BOSC23 (*Proc. Natl. Acad. Sci.* (*USA*) 90:8392–8396), PT67 (Miller and Miller. 1994. *J. Virol.* 68:8270–8276, Miller. 1996. *Proc. Natl. Acad. Sci.* (*USA*) 93:11407–11413), PA317 (*Mol. Cell Biol.* 6:2895 (1986)), PG13, 293 cells transfected with pIK6.1 packaging plasmids (U.S. Pat. No. 5,686,279), GP+envAM12 (*Virology* 167:400 (1988), PE502 cells (*BioTechniques* 7:980–990 (1989)), GP+86 (Markowitz, et al. 1988. *J. Virol.* 62:1120–1124), Ψ-Cre (Danos and Mulligan. 1988. *Proc. Natl. Acad. Sci.* (*USA*) 85:6460–6464). The preferred titer of recombinant retrovirus particles is about $10^5$–$10^7$ infectious particles per milliliter. If these titers cannot be achieved the virus also can be concentrated before use.

In addition to recombinant retrovirus systems, other viral packaging systems such as adenovirus-associated virus (AAV), adenovirus, Sindbis virus, Semliki Forest virus, Epstein Barr virus, herpes simplex virus, HIV, or vaccinia virus can be used. Each of these systems has a different host range and can be used to infect cells that are refractory to retrovirus expression (i.e., non-dividing cells). In the Sindbis virus system (Invitrogen, San Diego, Calif.), the oligonucleotides to be expressed are ligated into the multiple cloning site of a Sindbis virus DNA vector, e.g. pSinRep5, operatively linked to a Sindbis subgenomic promoter and polyadenylation site; the oligonucleotides replace the Sindbis virus structural protein genes. pSinRep5 includes an SP6 RNA polymerase promoter for the in vitro synthesis of recombinant Sindbis virus genomes; a packaging signal for recombinant RNA packaging; and the Sindbis nonstructural polyprotein gene open reading frame. For the production of Sindbis virus particles, the recombinant Sindbis vector encoding the oligonucleotide DNA is linearized, transcribed into RNA and co-transfected into vertebrate (BHK-21, Vero) or invertebrate cells (Drosophila) with RNA transcribed from the helper vector, pDH-BB, that encodes the viral structural proteins. Following transfection, the recombinant Sindbis genomic RNA acts as a mRNA, is translated into the Sindbis virus polymerase, and expresses the encoded ribozyme and the structural proteins from the helper RNA. Because of Sindbis virus' wide host range, the recombinant Sindbis virus can be packaged and used to express the ribozyme library in mammalian, avian, reptilian, insect cells (e.g., mosquito and Drosophila cells). See for example, Xong, C. et al. (1989) *Science* 243:1188–1191; Huang, H. V. et al. (1993) U.S. Pat. No. 5,217,879; Hahn C. S. et al. (1992) *Proc. Natl. Acad. Sci.* (USA) 89:2679–2683; Huang, M. and Sommers, J. (1991) *J. Virol.* 65:5435–5439.

For ribozyme expression in AAV, the oligonucleotide DNA is cloned into an AAV expression vector, such as ALAPSN, that contains a cloning site functionally linked to a promoter such as a Moloney leukemia virus promoter and flanked by AAV terminal repeats and a packaging signal, a means for selection. As an example, ALAPSN comprises a neomycin resistance gene functionally linked to SV40 transcription control elements. Similar AAV vectors, such as CWRSP and CWRSP.N, with comparable features also can be used. As an example, to produce recombinant AAV particles, 293 cells are infected with adenovirus type 5; then the infected cells are co-transfected with an ALAPSN plasmid-oligonucleotide DNA construct and an AAV helper plasmid, e.g. pAAV/Ad (Samulski et al., (1989) *J. Virol.* 63:3822–3828). As recombinant AAV is produced, the 293 cells undergo cytopathology, becoming spherical and lose their ability to adhere to a tissue culture surface. Following development of maximal cytopathology the supernatant and/or cell lysate is harvested and, if necessary, concentrated (Halbert et al. 1997. *J. Virol.* 71:5932–5941). Other methods for producing recombinant AAV also can be used, for example as described in U.S. Pat. No. 5,354,678. The combinatorial ribozyme library also can be expressed using adenovirus expression systems as described in U.S. Pat. No. 5,631,236, U.S. Pat. No. 5,670,488, WO94/28152, WO95/14091, EP0707071, WO96/05321, WO95/14101, WO95/14102, WO97/00326, EP94202322.7.

For vaccinia virus expression, a replication competent vaccinia virus can be used. The oligonucleotides to be expressed are operatively linked to a vaccinia virus promoter, for example, P11. In a preferred embodiment, vaccinia virus strain MVA is used because it expresses recombinant genes but contains a deletion that renders it replication incompetent in mammalian cells. Therefore, nucleic acids can be expressed in target host mammalian cells without the development of vaccinia virus induced cytopathology. The recombinant vaccinia virus strain MVA is produced by infecting chicken embryo fibroblasts (CEF) with vaccinia MVA and transfecting the transfer vector, pG01, into which has been ligated the ribozyme and a marker gene (beta galactosidase) functionally linked to a vaccinia promoter, such as P11, and flanked by the MVA genome sequences that flank the site of the MVA genomic deletion. The P11-ribozyme/beta-galactosidase construct is inserted into the MVA genome by homologous recombination. Recombinant viruses can be identified by in situ staining for beta-galactosidase expression with X-gal (Wyatt et al. (1995) *Virology* 210:202–205).

The combinatorial ribozyme library also can be expressed from plasmid expression vectors that are transfected directly into target host cells, including mammalian cells, although an intervening bacterial amplification step can be performed prior to delivery of the library to the target host cells. The direct delivery of the plasmid expression vector into the target host cells without an intervening bacterial cloning or transformation step is preferred because it provides a significant savings in time and expense and increases the number of genes and ribozyme libraries that can be studied. Expression plasmids contain cloning sites operatively linked to transcriptional regulatory elements functional in the target host cells. When the target host cells are mammalian cells, examples of transcriptional regulatory elements that can be used include SV40, CMV, metallothionein, or tetracycline transcriptional regulatory elements: pCEP4 (Invitrogen, San Diego, Calif.), pCMVb, (Clontech, Palo Alto, Calif.), pAlter®-MAX (Promega, Madison, Wis.). The plasmid preferably contains sequences to provide high-copy episomal replication and selectable markers for stable maintenance of the vector in the host cell. The plasmids containing the oligonucleotide DNA are transfected directly into the target cell of interest. To increase transfection efficiency, preferably the plasmids are supercoiled with a gyrase. The oligonucleotides encoding the combinatorial ribozyme library alternatively can be ligated into plasmids and functionally linked to the T7, SP6, T3 or a similar RNA polymerase promoter. The plasmid expression vectors that can be used include pGEM-3Z and pAlter® -Ex1 (Promega, Madison, Wis.). The plasmid-oligonucleotide DNA construct is transfected into mammalian cells that are infected with a vaccinia strain such as MVA that expresses the appropriate RNA polymerase (Wyatt et al., (1995) *Virology* 210:202–205). For the example of vaccinia MVA T7, the T7pol transcribes the oligonucleotides from the plasmid vector. The vaccinia MVA amplifies the plasmid-oligonucleotide DNA construct copy number, resulting in an increased intracellular template concentration for T7pol transcomplementation and increased ribozyme expression and thus activity.

Other systems for the expression of nucleic acids functionally linked to T7 RNA polymerase or other bacteriophage promoters (SP6 or T3) also can be used. Ribozyme expression can be performed with a recombinant retrovirus vector containing the oligonucleotides encoding the ribozyme functionally linked to a T7 RNA polymerase promoter (T7pro) and T7 terminator. This expression cassette is flanked by 5' and 3' LTRs, a packaging signal and includes the T7pol gene, that encodes a T7pol that contains a nuclear localization signal (T7pol-nls), functionally linked to a eukaryotic promoter. In this system, the expressed T7 protein is transported to the nucleus for transcription. Due to the high transcriptional activity of T7pol, high intracellular levels of ribozyme can be achieved. Optionally, the ribozyme can be fused to second ribozyme that acts intramolecularly to free the ribozyme targeting the mRNA of interest.

Transfection of nucleic acid (DNA or RNA) encoding the combinatorial ribozyme library into cells is required for either packaging of recombinant vectors into virus particles or direct transfection of plasmids that express the combinatorial ribozyme library into target host cells and can be mediated by a variety of chemicals including calcium-phosphate, polybrene, DEAE-dextran, and liposomes. The calcium-phosphate method includes incubating the target cell with a calcium phosphate-nucleic acid co-precipitate. Polycations such as polybrene (about 4–10 micrograms/ml), a polycation that acts by neutralizing the net negative surface charges on the virus and cells (Stoker. "Retroviral Vectors" In Molecular Virology: A Practical Approach, Davison and Elliott, eds., p 187), or DOSPER (Boehringer-Mannheim) also can be used to increase the efficiency of transfection of low molecular weight DNA. Liposomes are available from a variety of commercial suppliers and include DOTAP™ (Boehringer-Mannheim), Tfx™-50, Transfectam®, ProFection™ (Promega, Madison Wis.), and Lipofectamine™, Lipofectin®, LipofectAce™ (GibcoBRL, Gaithersburg, Md.). In solution, the lipids form vesicles that associate with the nucleic acid and facilitate its transfer into cells by fusion of the vesicles with cell membranes or by endocytosis. Alternatively, DNA can be introduced into cells by electroporation. Each of these systems differ in their transfection efficiency for a given cell line. If transfection conditions for a given cell line have not been established or are unknown, they can be determined empirically (Maniatis supra). The number of ribozymes expressed per cell depends on the multiplicity of infection for a virus vector or the amount of DNA transfected per cell for a plasmid vector.

From one to multiple ribozymes in a chosen delivery vector are introduced into the recipient cell. When a retrovirus vector is used, following preparation of recombinant retrovirus in a packaging cell, the recombinant retrovirus is used to infect a host cell containing a mRNA transcribed from a target nucleic acid encoding the motif of interest. The infected or transfected host cell is grown and the phenotype of the infected or transfected host cell is analyzed to determine any alterations in phenotype as compared to an uninfected or untransfected host cell. Optionally, infected or transfected cells are isolated or selected from the population of normal cells. Alterations in cell phenotype are then correlated so as to assign a function to a product coded for by the cleaved mRNA target. DNA encoding the ribozyme expressed in the host cell can be isolated and sequenced to identify the sequence of the target mRNA, the gene from which it is transcribed and the encoded protein. This can be done, for example, by PCRing the ribozyme encoding sequence for example, from cellular DNA, or reverse transcription-PCR of RNA, then sequencing the ribozyme encoding sequence from the viral or plasmid expression vector in the target cell.

The target host cell can be any cell of interest that expresses a disease associated phenotype or a phenotype that can be differentiated from a "normal" or control cell. To determine if a target nucleic acid encoding a motif of interest is required for the cellular phenotype, a ribozyme library designed to cleave the transcription product of the target nucleic acid is constructed and expressed in the target host cell(s) that are then assayed for an altered cell phenotype. The altered phenotype can be any phenotype which can be detected, for example modified cell growth, DNA synthesis, synthesis of a protein(s), chemical responsiveness, apoptosis, morphologic changes, cell viability, replication, differentiation, expression of biologically active compounds (e.g., steroids), proliferation, drug susceptibility, the expression of cell surface molecules such as receptor molecules and antigens. Proteins that regulate gene expression in cells also can be identified. For example, this can be accomplished by monitoring the expression of a reporter gene expressed from a promoter that is active in, for example, tumor cells in the presence of ribozymes targeted to an mRNA encoding a motif known to function as a DNA binding protein. Conversely, for the identification of proteins responsible for the maintenance of a normal cell phenotype, ribozymes can be constructed to mRNAs encoding proteins that contain a motif of interest and which are expressed in the normal cells which are then assayed for an altered phenotype. In either approach, proteins and genes associated with disease pathways or phenotypes can be identified.

In order to evaluate an alteration in cell phenotype, any of a variety of methods can be used, depending at least in part on the phenotype of interest and the function associated with the targeted motif. In host cells which amplify and express ribozymes, phenotypic change can be monitored directly. For example, if the function of a protein containing the targeted motif prevents apoptosis and it is inhibited by one or members of a combinatorial ribozyme library, the host cell undergoes specific types of morphologic changes, such as nuclear condensation and DNA fragmentation, following ribozyme expression. If the targeted motif is found in a protein that is involved in drug susceptibility, this function can be identified by monitoring cells for altered resistance or susceptibility to the particulr drug or drugs.

Combinatorial ribozymes also can be used for functionating cellular and viral motif containing genes that are involved in virus replication. Combinatorial ribozyme libraries can be targeted to mRNAs encoding protein motifs that are postulated to be involved in a virus' lifecycle. If the targeted motif is found in a protein that affected replication, virus titers or cytopathic effects may increase or decrease.

Various stains can be employed to determine whether the function of the targeted nucleic acid affects for example, cell viability or membrane permeability. If the targeted nucleic acid encoding the motif of interest affects cell cycle regulation and transformation this can be monitored by measuring the incorporation of a labeled nucleotide into the cell. Antibody-based assays can be employed to detect the presence or absence of a protein of interest such as a cell membrane receptor. Additional types of assays known to those of skill in the art can be employed depending on the phenotype or cellular property that is being analyzed.

Phenotypic change also can be monitored, for example, by evaluating ribozyme activity by comparing the targeted mRNA levels in cells expressing and cells that do not express one or more members of the combinatorial ribozyme library. Total cellular or cytoplasmic RNA can be purified by a variety of methods (Maniatis supra pp. 7.6–7.29) and analyzed by Northern or dot blot (Maniatis supra pp. 7.37–7.57). mRNA can be assayed by reverse transcription-PCR employing primers that flank the targeted cleavage site(s). The absence or decreased production of a PCR product is indirectly indicative of ribozyme activity (Baier et al. 1994. *Molecular Immunology* 31:923–932).

The methods and compositions of the subject invention can be used to identify the function of nucleic acids encoding proteins containing motifs of interest. Motif-directed ribozyme libraries can be designed and constructed to target virtually any sequence encoding a motif for which a conserved or nearly conserved sequence can be identified. Conserved sequences have been described for caspases and protein kinases. In addition many other classes of enzymes can similarly be targeted. A conserved sequence encoding a zinc-finger domain that is found in many proteins has been described. Similarly, a sequence conserved in integrins has been described. Therefore, it is possible to target motifs in numerous proteins including enzymes, adhesion molecules, signaling molecules and structural proteins having a variety of physiological functions including enzyme activity, protein synthesis, biological factor expression or regulatory effector function, which alter various cellular phenotypes or responses including changes in cellular proliferation kinetics, changes in cellular viability, resistance to facilitated cell death, resistance to antibiotics, magnetic separation, directed migration, and preferential adhesion.

Following the identification of cells that exhibit an altered cellular phenotype in response to expression of a ribozyme, the host cell having an altered cellular phenotype is isolated or selected for on the basis of expression of an appropriate marker, which can be for example, a cell surface molecule, a drug resistance protein, an enzyme, or a bioluminescent molecule. Cells also can be isolated using FACS sorting, magnetic separation techniques, drug selection, visual selection, or methods based on enzymatic activity.

DNA or RNA is isolated from the host cell by standard molecular biology techniques and can be PCR amplified for sequencing as an initial step towards characterization of the corresponding gene, transcription product and protein. For example, this can be done by PCR amplifying the ribozyme-coding region of the viral or plasmid vector that delivered the ribozyme to the cell. The primer pair used to amplify the ribozyme sequence is derived from the vector sequences flanking the ribozyme insert. The PCR product is then sequenced to determine the mRNA sequence targeted by the ribozyme(s). Based on this information, the entire gene sequence can be determined and the sequence of the encoded protein can be deduced. PCR products also can be cloned into vectors for further analysis, or used as probes for identification of target nucleic acids.

In the following examples, a combinatorial ribozyme library is targeted to a zinc finger motif, C-X-X-C. Included in the library, at an equivalent proportion to the other components, is a ribozyme targeting green fluorescent protein (GFP). Green fluorescent protein (GFP) from the firefly Aequorea victoria emits bright green light upon exposure to UV light without the requirement of additional proteins, substrates, or cofactors. EGFP encodes a protein that has a single, red shifted spectrum and increased expression relative to GFP, and therefore, is easily monitored in living cells by fluorescence microscopy and fluorescence-activated cell sorting (FACS).

To demonstrate that the combinatorial ribozyme library can be used to inactivate genes involved in a given phenotype, the library targeting the zinc finger motif and containing the EGFP-targeted ribozyme is introduced into CHO-AA8 Tet-Off cells or 293 Tet-Off cells (Clontech, Palo Alto, Calif.) that express EGFP. Ribozyme activity is inversely proportional to reporter gene signal. Alternatively, the zinc finger motif can be incorporated into the EGFP sequence, expressed in either cell type described above, and inactivated by the combinatorial ribozyme library. Other reporter genes, for example chloramphenicol acetyltransferase (CAT), beta-galactosidase, or alkaline phosphatase, also can be used.

Kits containing combinatorial anti-motif ribozyme libraries also are provided. The containers of kit can contain a combinatorial library directed to motifs either as individual members of the library, or as a complete library. Optimally the kit contains vectors including plasmid vectors, retrovirus expression vectors and adeno-associated virus expression vectors for cloning the library. Additional components of the kit can include antibodies for recognition of a marker protein and PCR primers for amplification of the nucleotides encoding the ribozymes.

The following examples are offered by way of illustration and not by way of limitation.

EXAMPLES

Example 1

Design of Combinatorial Ribozyme Library to a Zinc Finger Motif

The following example discloses methods to design double stranded DNA ligonucleotides that code for a combinatorial hammerhead ribozyme library targeted to the zinc finger motif, C-X-X-C (X=any amino acid). Hammerhead ribozymes contain two recognition domains that are complementary to the mRNA encoding the motif of interest. Each recognition domain is composed of at least 6 nucleotides flanking both ends of the catalytic core. The optimum cleavage site of the target mRNA is a U. Based on these considerations the minimal target sequence contained in the coding sequence of the motif and cleavable by a ribozyme is determined. Also, considered is the known degeneracy of the genetic code. Mammalian codon usage may also be considered. Thus, for the zinc finger motif, described above with the amino acid sequence. C-X-X-C, the sequence is first reverse translated to: 5'-UGY-NNN-NNN-UGY (SEQ ID NO:32) (N=any nucleotide, Y=C or U). The amino acid sequence is scanned for amino acids that are preferably found at or near the middle of the motif that are coded for by codons that contain a U as a fixed position. In this case none are available, therefore, to target a ribozyme library to this sequence requires fixing one of the variable residues as a U and extending the recognition sequence arms of the ribozyme 5' and 3' from this position to include the less or invariable elements characteristic of the sequence. Taking into consideration that the hammerhead ribozyme contains two recognition sequences each comprised of 6 nucleotides, the minimal recognition sequence of the zinc motif is: 5'-NUGYNU<u>N</u>NNNUGY (SEQ ID NO:33) wherein NU<u>N</u>= cleavage recognition site, with cleavage occurring 3' to the underlined nucleotide. The underlined nucleotide is not targeted by the ribozyme because it does not hybridize or anneal with the binding sequences of the ribozyme. The structure of the ribozyme annealed to the target sequence is shown in FIG. 1.

The number of ribozymes targeting the minimum sequence is calculated by multiplying the number of nucleotides that may occupy each position of the binding regions. Omitted from this calculation is the nucleotide 5' to the cleavage site (underlined nucleotide) because it is not part of the ribozyme binding region. For the above example, the number of ribozymes to be made equals: 4×1×1×2×4×1×4× 4×4×1×1×2=4096.

Oligonucleotides encoding the combinatorial ribozyme library to the zinc finger motif are made in a 96-well matrix using parallel array technology and annealed to form double stranded DNA with unique Hind III and Cla I sites at each of the 5' and 3' ends, respectively, for ligation into a retrovirus vector. The general structure of two complementary oligonucleotides of the combinatorial library is as follows, with the catalytic core of a hammer head ribozyme in bold. The underlined regions are the ribozyme binding sequences when expressed as RNA that are complementary to all possible permutations of a mRNA sequence encoding the zinc finger motif (SEQ ID NO:34–35).

5' AGCTT<u>RCANNNC</u>TGATGAGTCCGTGAGGAC-GAA<u>ANRCANAT</u> 3'

3' <u>AYGTNNNG</u>ACTACTCAGGCACTCCT-GCTTT<u>NYGTNTAGC</u>5'

For annealing, approximately 1.0 microgram of each complementary oligonucleotide is dissolved in water and mixed at a one to one molar ratio in a 96-well microtiter plate at room temperature. The 5' end (left end) of the double stranded DNA fragment overlaps with an Hind III restriction enzyme site. The 3' end of the fragment (right end) overlaps with a Cla I site.

Example 2

Preparation of a Family of Retrovirus Plasmid Vectors

The purpose of this experiment is to prepare a retrovirus plasmid vector library containing the double stranded oligonucleotide DNA encoding the combinatorial ribozyme library to the zinc finger motif described in Example 1, supra. pLNCX, (50 micrograms, Clontech, Palo Alto, Calif.), which contains an extended viral packaging signal, multiple cloning site and neomycin resistance gene flanked by the Moloney murine leukemia virus 5' and 3' long terminal repeats and an ampicillin resistance gene is digested with restriction enzymes, Hind III and Cla I. Approximately, 0.5 to 2 μg of digested plasmid is placed into a well of a multi-well (e.g. 96 well) plate. The library of annealed oligonucleotides prepared in Example 1, supra, are added individually at 4 to 6 fold excess of the Hind III/Cla I treated pLNCX. The oligonucleotide DNA is ligated into pLNCX by adding a tenth volume of 10×T4 DNA ligation buffer and T4 DNA ligase. The final concentration of the ligation buffer components and T4 DNA ligase are: 0.05 M Tris-HCl (pH 7.6), 10 mM MgCl$_2$, 10 mM dithiothreitol (DTT), 50 µg/ml bovine serum albumin (Fraction V; optional), 1.0 MM ATP, 0.05 Weiss units of bacteriophage T4 DNA ligase per microliter. The ligation is performed for 4–8 hours at 16° C.

Also prepared, is a retrovirus vector encoding a known, active anti-EGFP ribozyme following the identical protocol.

Example 3

Transfection of Mammalian Cells Using Retrovirus Plasmid Vectors

The purpose of this experiment is to package the retrovirus plasmid vector library prepared in Example 2, supra, and an identical retrovirus plasmid containing a specific anti-EGFP ribozyme in retrovirus particles. Using a calcium phosphate precipitation method (Keck, et al. (1990) Cell 61:801–809, Cochran, et al. (1985) Proc. Natl. Acad. Sci. (USA) 82:19–23) for transfecting DNA into mammalian cells, 0.1 to 0.5 micrograms of ligated plasmid/oligo DNAs from Example 2, supra, is transfected into approximately 1,000 to 25,000 PT67 cells per well of a 96-well plate cultured in 100 µl of minimal essential media (MEM) supplemented with 10% fetal calf serum (FCS). Four hours later the media is replaced with fresh MEM supplemented with 10% FCS and incubated at 37° C. for 48 hours. The retrovirus vector contains a neomycin resistance gene; therefore. G418 selection is used to obtain a population of cells that stably express the transfected vector and to monitor virus titers. Recombinant retrovirus production is monitored by titering aliquots of the transfected cell supernatant in a focus forming assay in which cells infected with the recombinant retrovirus become resistant to G418 (Clontech, Palo Alto, Calif.). When virus titers >$10^5$/ml are reached, usually between 2–7 days, the viruses are harvested, and random pools of retroviruses containing the combinatorial library and the specific EGFP ribozyme are made. These pools are used to infect into target cells, CHO-AA8-Tet-Off cells (Clontech, Palo Alto, Calif.), expressing EGFP (CHO-EGFP) seeded into 96-well plates. Alternatively, the packaged retrovirus library is titered and infected into fresh PT67 cells at a multiplicity of 1. These cells are counted then added to multi-well dishes seeded with target cells. The ratio of retrovirus producing PT67 cells and targets cells can vary from about 1 to 10. As the retrovirus particles emerge from the PT67 cells, the CHO-EGFP cells are infected.

Example 4

Analysis of Ribozyme Activity

This experiment is designed to demonstrate that a ribozyme in a combinatorial library an inactivate its mRNA resulting in an altered phenotype of the target host cell. In this experiment, ribozyme activity is inversely proportional to EGFP expression. The ribozyme hybridizes to and cleaves the EGFP mRNA, thereby, reducing EGFP protein expression.

CHO-EGFP cells (Clontech, Palo Alto, Calif.) are cultured to near confluency or approximately 50,00–75,000 cells per well of a 96-well plate in MEM with 10% FCS. The recombinant retroviruses library containing the retrovirus encoding the anti-GFP ribozyme from Example 3, supra, are randomly pooled and used to infect the cultures of CHO-EGFP cells. The multiplicity of infection (virus particle per cell ratio) is about 5–10 to insure that every cell per well is infected with at least one virus particle. Infection of target cells is enhanced with polybrene (generally 10 micrograms/ml). Mock infected cells or parental CHO cells that do not express EGFP serve as controls. Following infection, the cells are incubated for 48 hours at 37° C. and then assayed for EGFP expression.

EGFP expression is assayed by EGFP fluorescence using an incident light at 488 nm and measuring the emitted light at 507 nm. The emitted or observed light is detected using the appropriate set of filters, corresponding to the wavelength of the incident and emitted light with a Wallac-Victor Fluorometer or by a Fluorescence Activated Cell Sorter (FACS). Cells with decreased EGFP production were analyzed by PCR to confirm the presence of the EGFP-specific ribozyme.

Example 5

Preparation of Plasmid Vector for Non-Retroviral Transfection

This example discloses the construction of plasmid vectors that express the combinatorial ribozymes. The oligonucleotide ribozyme library containing the anti-EGFP ribozyme is ligated into the multiple cloning site of pCEP4 (Invitrogen, San Diego, Calif.) operatively linked to the CMV promoter and SV40 polyadenylation signal. pCEP4 is an Epstein Barr virus (EBV)-based vector that is maintained extrachromosomally in primate and canine cell lines. pCEP4 contains the nuclear antigen, EBNA-1, for high-copy episomal replication of the plasmid by the EBV origin of replication, oriP, and the hygromycin resistance gene for stable maintenance of the vector. In this example, the oligonucleotides are designed to contain Hind III and BamH I sites to facilitate ligation into the expression vector. The anti-EGFP ribozyme is synthesized and cloned as described for the combinatorial ribozyme library but also containing Hind III and BamH I sites. The synthesis, annealing and ligation procedures are the same as those described for the retrovirus vectors in Example 2, supra.

Example 6

Transfection of Mammalian Cells (Non-Retroviral-Mediated Transfection

This experiment demonstrates the delivery of plasmid DNA encoding the EGFP ribozyme and the combinatorial ribozyme library to mammalian cells. Random pools of pCEP4 DNAs containing the EGFP ribozyme and the combinatorial library are introduced into host cells by calcium-phosphate precipitation (Cochran et al. (1985) Proc. Natl. Acad. Sci. (USA) 82:19–23, Keck et al. (1990) Cell 61:801–809). The pCEP4 DNA was treated with gyrase (Mizuuchi et al. (1984) J. Biol. Chem. 259:9199–9201; Bates et al. (1996) Biochemistry 35:1408–1416) to increase the transfection efficiency. Gyrase treatment is carried out for 1 hour at 25° C. in 35 mM Tris-HCl (pH 7.5), 24 mM KCl, 4 mM MgCl$_2$, 1.8 mM spermidine, 9 microgram/ml tRNA, 5 mM dithiothreitol, 6.5% (w/v) glycerol, 100 microgram/ml bovine serum albumin, 12 nM gyrase, 1 mM ATP (Bates et al. 1996. Biochemistry 35:1408–1416). In either case, by increasing the amount of transfected DNA from the ligation reaction, more than one ribozyme targeted to a specific sequence is transfected per cell. This increases the probability that the target mRNA is inactivated and an altered phenotype is produced.

Example 7

Analysis of Ribozyme Activity

This experiment is designed to demonstrate the inactivation of EGFP expression in target cells transfected with plasmid vectors that express the combinatorial ribozyme library and the EGFP mRNA. Ribozyme activity is inversely proportional to EGFP expression. The ribozyme hybridizes to and cleaves the EGFP mRNA, thereby, reducing EGFP protein expression. EGFP is assayed as described above and the presence of the anti-EGFP ribozyme is confirmed according to the procedure described in Example 4, supra.

CHO-EGFP cells (Clontech, Palo Alto, Calif.) are cultured to near confluency in 96-well plates in MEM supplemented with 10% FCS as described in example 4, supra. The plasmids for expression of the combinatorial ribozyme library and the anti-EGFP ribozyme from Example 6, supra, are randomly pooled and used to transfect CHO-EGFP cells. Approximately, 0.1–0.5 micrograms of plasmid DNA are used to transfect approximately each well of the CHO-EGFP cells cultured in 96-well microtiter dishes to insure that every cell was transfected with at least one plasmid. Mock transfected cells or parental CHO cells serve as controls. Following transfection, the CHO-EGFP cells are incubated for 48–72 hours. EGFP is assayed as described in Example 4, supra.

Example 8

Design of a Combinatorial Ribozyme Library to the Receptor Protein Kinase Motif The following example discloses methods to design double stranded DNA oligonucleotides that code for a combinatorial hammerhead ribozyme library targeted to the receptor protein kinase motif, G-X-H-X-N-[LIVM]-V-N-L-L-G-A-C-T (X=any amino acid; [ ]=position contains one of the enclosed amino acids). The sequence is first scanned for amino acids that are preferably found at or near the middle of the motif that are coded for by codons that contain a U as a fixed position. In this particular case the position containing Leucine (L), Isoleucine (I), Valine (V) or Methionine (M) is coded for by nucleotides as follows:

| L:CUA | I:AUA | V:GUA | M:AUG |
| --- | --- | --- | --- |
| CUC | AUC | GUC | |
| CUG | AUU | GUG | |
| CUU | | GUU | |
| UUA | | | |
| UUG | | | |

Thus, L, I, V or M could be coded for by a codon of the sequence: NUN (N=any nucleotide). Hence, a U is fixed in the second position of this codon and can be used as part of a ribozyme cleavage site. As described in Example 1, supra, if a fixed U residue can not be found in the motif, one can be fixed into a variable position.

Taking into consideration that the hammerhead ribozyme contains recognition sequences comprised of 6 nucleotides and codon degeneracy, the minimal motif target is, X-N-[LIVM]-V-N (SEQ ID NO:36), which is reverse translated to yield the minimal nucleotide target for the combinatorial ribozyme library: 5'-N-A-A-Y-N-U-N-G-U-N-A-A-Y (SEQ ID NO: 37) wherein N=any nucleotide; Y=C or U; NU$\underline{N}$= ribozyme cleavage site, with cleavage occurring 3' to the underlined nucleotide. The underlined nucleotide is not targeted by the ribozyme because it does not hybridize or anneal with the binding sequences of the ribozyme. The number of individual ribozymes necessary to target all possible nucleotide combinations that may be translated into the motif is calculated as described in Example 1: 4×1×1× 2×4×1×1×1×4×1×1×2=256. The general sequence of the expressed combinatorial ribozyme library is (SEQ ID NO:38):

5'-<u>RUUNAC</u>CUGAUGAGUCCGUGAGGACGAA <u>ANRUUN</u>

(R=G or A). The underlined regions are the ribozyme binding sequence when expressed as RNA that are complementary to the mRNA encoding the receptor protein kinase motif and the bold region is the catalytic core of the ribozyme. Other ribozyme libraries also can also be targeted to other regions of this motif using the guidelines described above.

Example 9

Design of a Combinatorial Ribozyme Library to the Integrin Motif

The following example discloses methods to design oligonucleotides that code for a combinatorial hammerhead ribozyme library targeted to the integrin motif: C-X-[GNQ]-X(1,3)-G-X-C-X-C-X(2)-C-X-C (SEQ ID NO:39). Following the guidelines described in Examples 1 and 8, the G-X-C-X-C (SEQ ID NO:40) can be easily targeted where the amino acid, C (Cysteine), is encoded by UGU or UGC and the amino acid, G (Glycine) is encoded by GGN. Therefore the following mRNA sequence can be targeted: 5'-GNNNNU<u>G</u>YNNNUG (SEQ ID NO:41). The general sequence of the oligonucleotides encoding the combinatorial ribozyme are (SEQ ID NO:42):

5'-<u>CANNNR</u>CTGATGAGTCCGTGAGGACGAA <u>ANNNNC</u>.

The underlined regions and bold region are the ribozyme binding sequences and catalytic core, respectively. The number of ribozymes necessary to target all possible nucleotide combination is 32,768. Other ribozyme libraries also can be targeted to other regions of this motif using the guidelines described above.

Example 10

Isolation of Cells Expressing a Selectable Marker Associated With a Ribozyme Expressing Construct The following experiment demonstrates the ability to isolate cells expressing a selectable marker associated with a ribozyme expressing construct from cell cultures transduced with a library of pooled ribozymes. A pool of ribozymes directed against the lck gene was synthesized using oligonucleotides encoding a hammerhead ribozyme catalytic core flanked by nucleotide sequences complementary to sequences in the lck mRNA. Specific restriction endonuclease sites were also engineered into the oligonucleotides to facilitate directional cloning and recovery of ribozyme sequences. Sense and antisense oligonucleotides were annealed to form a double stranded DNA which was then ligated into an AAV based plasmid vector using T4 ligase in a manner similar to that described in Example 2. DNA constructs encoding at least 12 different ribozyme molecules cloned into AAV plasmid vectors were transfected into a virus packaging cell line, and recombinant virus was harvested from the supernatant in a manner similar to the one outlined in the Preferred Embodiments (page 16, lines 23–29). The resulting recombinant virus was then used to infect the Jurkat T-cell leukemia line. Infected cultures were harvested and stained with a fluorescently labelled antibody (Pharmingen, San Diego, Calif.) directed against the selectable (Lyt-2/CD8a) marker. Marker expression on the cells was then analyzed by flow cytometry. This analysis revealed a small population of marker bearing cells present in the population (see FIG. 3A). This population of cells was isolated using fluorescence activated cells sorting and expanded in culture using RPMI 1640 tissue culture medium (Life Technologies, Grand Island, Utah) according to standard cell culture techniques. Upon re-analysis by the same method, 100% of the sorted population was found to express the selectable marker (see FIG. 3B), suggesting that the recombinant ribozyme-expressing AAV genome had been stably integrated into the host cell genome. These results demonstrate that cells expressing ribozyme constructs can be isolated and separated from those that do not and that these cells can be expanded in culture for further analysis of cell phenotype or responsiveness.

Example 11

Isolation of a Population of Cells Which Have Lost a Specific Cellular Response

Figure 4A:
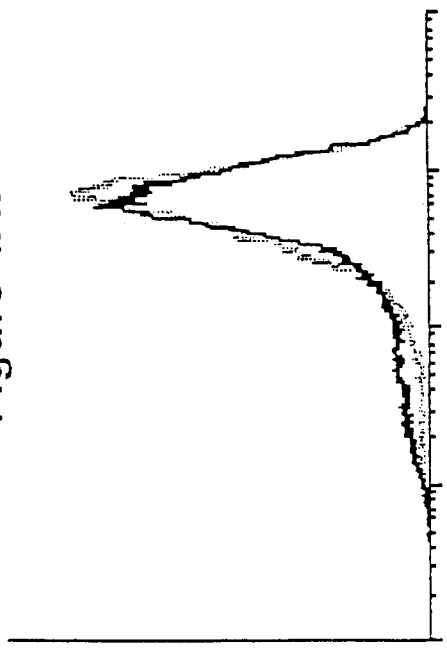
FIG. 4 demonstrates the effect of expressing a library of ribozymes on the induction of a cellular protein by cells in a culture. Loss of the ability to induce the protein exemplifies the loss of a cellular response in ribozyme-expressing cells. The X axis depicts expression of the induced protein. The Y axis depicts cell number. The histogram in FIG. 4A shows the profile of induced protein expression in normal cultures (stippled lines) or in cultures expressing a library of pooled ribozymes (solid lines). The histogram in FIG. 4B shows the same histogram with an expanded y-axis to reveal the leftward shifting population of cells, corresponding to those cells which have lost the ability to induce the protein. Cells from the leftward part of the histogram in FIGS. 3A and B were isolated by flow cytometric cell sorting, grown in culture, and induction of the cellular protein was re-analyzed. The histogram in FIG. 4C demonstrates that the subpopulation of cells which have lost the responsive phenotype (represented by the left-hand peak of the histogram) can be enriched from cultures expressing several different ribozyme species represented in the original pooled library.
Figure 4B:
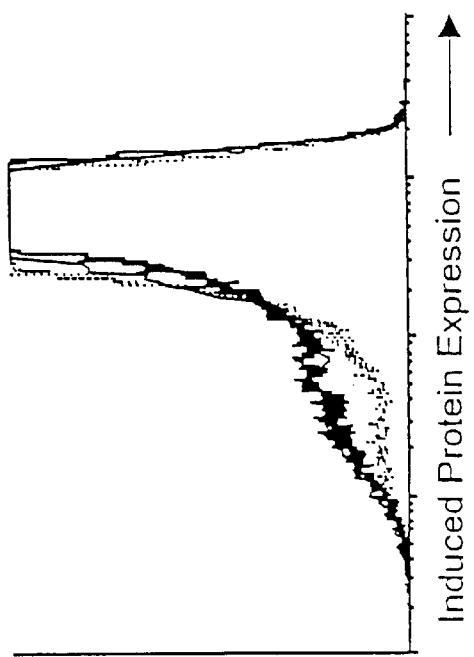

This experiment demonstrates that a population of cells that have lost a specific cellular response can be isolated from a culture of cells expressing a library of pooled ribozymes. Jurkat cells expressing the AAV/ribozyme plasmid selectable marker (Lyt-2/CD8a) derived from the experiment described in Example 10 were stimulated through T-cell receptor engagement with anti-CD3 plus anti-CD28 (Pharmingen, San Diego, Calif.) (Weiss et al., (1991) *Semin. Immunol.*, 3:313–324; Abraham et al., (1992) *Trends Biochem. Sci.*, 17: 434–438), for 40 hours, and the induction of CD69, a cell surface activation protein whose expression is dependent upon Lck protein kinase function (Goldsmith and Weiss, (1987) *Proc. Natl. Acad. Sci. USA*, 84:6879–6883; Straus and Weiss, (1992) *Cell*, 70:585–593) was analyzed by flow cytometry using a fluorescently labeled antibody (Pharmingen, San Diego, Calif.). This analysis showed that a fraction of ribozyme containing cells had lost the ability to induce the activation related protein following cell stimulation (see FIG. 4A). This population of unreactive cells was isolated using fluorescence activated cell sorting and recultured. Upon re-analysis, an enrichment of the unresponsive population was observed. These results show that a population of cells with a specific altered phenotype or response can be isolated from a culture of cells expressing a library of pooled ribozymes directed against a specific gene. In this particular example, unresponsive cells were isolated from the rest of population using flow cytometry.

Example 12

Recovery of Ribozyme Sequences From Altered Cells Which Express a Library of Pooled Ribozymes This experiment demonstrates that ribozyme sequences can be recovered from cells which express a library of pooled ribozymes and which have an altered phenotype or response, and that only a limited number of ribozyme species are recovered as compared to the number of species present in the original library of pooled ribozymes. Jurkat cells derived from the experiment described in Example 11 which had been sorted for the lack of specific protein induction were lysed in 1×Taq PCR buffer/0.45% NP-40/0.45% TWEEN®-20, and ribozyme sequences were amplified from cellular DNA in a standard PCR reaction using 1×Taq PCR buffer/1.5 mM MgCl$_2$/200 µM dNTPs/0.2 µM oligonucleotide primers/0.625U Taq polymerase (Promega, Madion, Wis.). Amplification was performed for 30 cycles, using a melting temperature of 94° C. for 30 seconds per cycle, an annealing temperature of 60° C. for 30 seconds per cycle, and an extension temperature of 72° C. for 45 seconds per cycle. A final incubation of 72° for seven minutes followed by the final amplification cycle. The primer pair used to amplify the ribozyme sequences was derived from the AAV plasmid vector sequences flanking the ribozyme insert, and had the sequence 5'-ATCCGCGTCCTAGGCACGTGA-3' (SEQ ID NO: 44) and 5'-GTTACTAGTCCGCGGCTCGAC-3' (SEQ ID NO: 45). PCR products containing ribozyme sequences were cloned into pCR2.1-TOPO (Invitrogen, Carlsbad, Calif.). Cloned DNAs were transformed into bacteria and the transformed bacteria were plated on LB-agar/amp plates. Colony purified ribozyme clones were then sequenced, and the identities of the ribozymes associated with the loss of cell responsiveness were ascertained. While the original library of pooled ribozyme sequences consisted of 12 or more individual ribozyme specifies, the majority of clones (42/45) sequenced contained ribozymes of a single species. Only one other ribozyme species was represented in this particular analysis (3/45 clones). These results indicate that isolation of specific ribozyme sequences associated with the loss of a specific cell phenotype or response is possible, even when these ribozyme sequences constitute a minor component of a larger library of pooled ribozymes. Knowledge of the specific ribozyme sequences associated with the loss of cellular function can be used to clone and/or identify previously known or unknown cellular genes involved in generating a specific cellular phenotype or response using standard molecular biologic techniques.

The above examples describe methods and compositions for construction of a combinatorial ribozyme library and its high throughput delivery and intracellular expression to determine the function of a product(s) encoded by a target nucleic acid that contains a motif of interest. Methods are described for design of oligonucleotides that encode a combinatorial ribozyme library to nucleic acids encoding proteins containing a motif of interest, the construction of vectors that express nucleic acids that encode a combinatorial ribozyme library; the ligation of the oligonucleotides into retrovirus vectors, other viruses, or plasmid vectors; the packaging of the recombinant vector into virus particles; the expression of the encoded library from cells either infected with the virus particles or cells directly transfected without a bacterial amplification step with the recombinant plasmid expression vectors. The results demonstrate that a combinatorial ribozyme library expressed from either recombinant virus or recombinant plasmid expression vectors inactivate a target nucleic acid to produce an altered cellular phenotype, and that both the specific ribozyme species and the targeted cellular gene associated with that altered cellular phenotype can be identified, so that a function can be assigned to the target nucleic acid.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now having been fully described, it will be apparent to one of ordinary skill in the art that many changes and modifications can be made thereto without departing from the spirit or scope of the appended claims.

What is claimed is:

1. A method of assigning a function to a target nucleic acid comprising a nucleotide sequence encoding a motif of interest, said method comprising the steps of:
   growing a host cell culture comprising host cells that express ribonucleic acid molecules encoded by a combinatorial ribozyme library, wherein:
      each said ribonucleic acid molecule comprises a binding region complementary to a transcription product of said target nucleic acid, and a catalytic domain that cleaves a sequence within said transcription product of said target nucleic acid that encodes said motif of interest so that expression of said transcription product is disrupted and an altered host cell is produced;
   a function of the target nucleic acid or encoded product is unknown;
   the combinatorial ribozyme library comprises nucleic acids encoding a plurality of the ribonucleic acid molecules each containing a recognition sequence for one of a plurality of degenerate sequences based upon a consensus nucleotide sequence encoding the motif;
   detecting phenotypic changes in the altered host cell; and
   correlating the phenotypic changes in said altered host cell, as compared to a control host cell, with the identity of said target nucleic acid by isolating DNA from said altered host cell and determining a specific ribozyme sequence contained therein that contains a binding sequence that is complementary to a transcription product of the target nucleic acid, whereby a function for said target nucleic acid is assigned based upon said phenotypic changes in said altered host cell.

2. The method according to claim 1, wherein said function is a physiological function.

3. The method according to claim 1, wherein said function is enzyme activity.

4. The method according to claim 1, wherein said function is protein synthesis.

5. The method according to claim 1, wherein said function is biological factor expression.

6. The method according to claim 1, wherein said function is membrane permeability.

7. The method according to claim 1, wherein said function is a regulatory effector function.

8. The method according to claim 7, wherein said regulatory effector function affects induction of a physiological function.

9. The method according to claim 1, wherein said function is altered directly.

10. The method according to claim 1, wherein said host cell culture comprises a plurality of mammalian cells, bacterial cells, invertebrate cells or plant cells.

11. The method according to claim 1, wherein said motif is a zinc finger motif, a receptor protein kinase motif, or an integrin motif.

\* \* \* \* \*

SEQUENCE LISTING (1) GENERAL INFORMATION:

(iii) NUMBER OF SEQUENCES: 45

(2) INFORMATION FOR SEQ ID NO: 1:

(i) SEQUENCE CHARACTERISTICS:
          (A) LENGTH: 19 base pairs
          (B) TYPE: nucleic acid
          (C) STRANDEDNESS: single
          (D) TOPOLOGY: linear (ii) MOLECULE TYPE: other nucleic acid (xi) SEQUENCE DESCRIPTION: SEQ ID NO: 1:

NNNNNNNUGY NUNNNNUGY                                                    19

(2) INFORMATION FOR SEQ ID NO: 2:

(i) SEQUENCE CHARACTERISTICS:
          (A) LENGTH: 34 base pairs
          (B) TYPE: nucleic acid
          (C) STRANDEDNESS: single
          (D) TOPOLOGY: linear (ii) MOLECULE TYPE: other nucleic acid (xi) SEQUENCE DESCRIPTION: SEQ ID NO: 2:

RCANNNCUGA UGAGUCCGUG AGGACGAAAN RCAN                                   34

(2) INFORMATION FOR SEQ ID NO: 3:

(i) SEQUENCE CHARACTERISTICS:
          (A) LENGTH: 36 base pairs
          (B) TYPE: nucleic acid
          (C) STRANDEDNESS: single
          (D) TOPOLOGY: linear (ii) MOLECULE TYPE: other nucleic acid (xi) SEQUENCE DESCRIPTION: SEQ ID NO: 3:

CCAGCTCCTG ATGAGTCCGT GAGGACGAAA CCAGGA                                 36

(2) INFORMATION FOR SEQ ID NO: 4:

(i) SEQUENCE CHARACTERISTICS:
          (A) LENGTH: 36 base pairs
          (B) TYPE: nucleic acid
          (C) STRANDEDNESS: single
          (D) TOPOLOGY: linear (ii) MOLECULE TYPE: other nucleic acid (xi) SEQUENCE DESCRIPTION: SEQ ID NO: 4:

GGCCGTTCTG ATGAGTCCGT GAGGACGAAA CGTCGC                                 36

(2) INFORMATION FOR SEQ ID NO: 5:

(i) SEQUENCE CHARACTERISTICS:
          (A) LENGTH: 36 base pairs
          (B) TYPE: nucleic acid
          (C) STRANDEDNESS: single
          (D) TOPOLOGY: linear (ii) MOLECULE TYPE: other nucleic acid (xi) SEQUENCE DESCRIPTION: SEQ ID NO: 5:

```
CTCGCCGCTG ATGAGTCCGT GAGGACGAAA CACGCT                           36

(2) INFORMATION FOR SEQ ID NO: 6:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 6:

GCAGATGCTG ATGAGTCCGT GAGGACGAAA CTTCAG                           36

(2) INFORMATION FOR SEQ ID NO: 7:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 7:

TGGTCACCTG ATGAGTCCGT GAGGACGAAA GGGTGG                           36

(2) INFORMATION FOR SEQ ID NO: 8:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 8:

AGCGGCTCTG ATGAGTCCGT GAGGACGAAA GGCACT                           36

(2) INFORMATION FOR SEQ ID NO: 9:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 9:

CATGGCGCTG ATGAGTCCGT GAGGACGAAA CTTGAA                           36

(2) INFORMATION FOR SEQ ID NO: 10:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 10:

GCTCCTGCTG ATGAGTCCGT GAGGACGAAA CGTAGC                           36
```

-continued (2) INFORMATION FOR SEQ ID NO: 11:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 11:

CGTCCTTCTG ATGAGTCCGT GAGGACGAAA AGAAGA                              36

(2) INFORMATION FOR SEQ ID NO: 12:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 12:

CGCCCTCCTG ATGAGTCCGT GAGGACGAAA ACTTCA                              36

(2) INFORMATION FOR SEQ ID NO: 13:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 13:

TGCGGTTCTG ATGAGTCCGT GAGGACGAAA CCAGGG                              36

(2) INFORMATION FOR SEQ ID NO: 14:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 14:

CCTCCTTCTG ATGAGTCCGT GAGGACGAAA AGTCGA                              36

(2) INFORMATION FOR SEQ ID NO: 15:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 15:

GTAGTTGCTG ATGAGTCCGT GAGGACGAAA CTCCAG                              36

(2) INFORMATION FOR SEQ ID NO: 16:

(i) SEQUENCE CHARACTERISTICS:
        (A) LENGTH: 36 base pairs (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 16:

TGATATACTG ATGAGTCCGT GAGGACGAAA CGTTGT                              36

(2) INFORMATION FOR SEQ ID NO: 17:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 17:

GGATCTTCTG ATGAGTCCGT GAGGACGAAA AGTTCA                              36

(2) INFORMATION FOR SEQ ID NO: 18:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 18:

GGTCGGCCTG ATGAGTCCGT GAGGACGAAA GCTGCA                              36

(2) INFORMATION FOR SEQ ID NO: 19:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 19:

GCAGCAGCTG ATGAGTCCGT GAGGACGAAA CGGGGC                              36

(2) INFORMATION FOR SEQ ID NO: 20:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 20:

CAGGGCGCTG ATGAGTCCGT GAGGACGAAA CTGGGT                              36

(2) INFORMATION FOR SEQ ID NO: 21:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 21:

CCAGCAGCTG ATGAGTCCGT GAGGACGAAA CCATGT             36

(2) INFORMATION FOR SEQ ID NO: 22:

(i) SEQUENCE CHARACTERISTICS:
             (A) LENGTH: 36 base pairs
             (B) TYPE: nucleic acid
             (C) STRANDEDNESS: single
             (D) TOPOLOGY: linear (ii) MOLECULE TYPE: other nucleic acid (xi) SEQUENCE DESCRIPTION: SEQ ID NO: 22:

CCATGCCCTG ATGAGTCCGT GAGGACGAAA GAGTGA             36

(2) INFORMATION FOR SEQ ID NO: 23:

(i) SEQUENCE CHARACTERISTICS:
             (A) LENGTH: 14 amino acids
             (B) TYPE: amino acid
             (C) STRANDEDNESS: not relevant
             (D) TOPOLOGY: linear (ii) MOLECULE TYPE: peptide (xi) SEQUENCE DESCRIPTION: SEQ ID NO: 23:

Gly Xaa His Xaa Asn Xaa Val Asn Leu Leu Gly Ala Cys Thr
1               5                   10

(2) INFORMATION FOR SEQ ID NO: 24:

(i) SEQUENCE CHARACTERISTICS:
             (A) LENGTH: 12 amino acids
             (B) TYPE: amino acid
             (C) STRANDEDNESS: not relevant
             (D) TOPOLOGY: linear (ii) MOLECULE TYPE: peptide (xi) SEQUENCE DESCRIPTION: SEQ ID NO: 24:

Lys Pro Lys Xaa Xaa Xaa Xaa Gln Ala Cys Xaa Gly
1               5                   10

(2) INFORMATION FOR SEQ ID NO: 25:

(i) SEQUENCE CHARACTERISTICS:
             (A) LENGTH: 13 amino acids
             (B) TYPE: amino acid
             (C) STRANDEDNESS: not relevant
             (D) TOPOLOGY: linear (ii) MOLECULE TYPE: peptide (xi) SEQUENCE DESCRIPTION: SEQ ID NO: 25:

His Xaa Xaa Xaa Xaa Xaa Xaa Xaa Xaa Xaa Xaa His Gly
1               5                   10

(2) INFORMATION FOR SEQ ID NO: 26:

(i) SEQUENCE CHARACTERISTICS:
             (A) LENGTH: 10 amino acids
             (B) TYPE: amino acid
             (C) STRANDEDNESS: not relevant
             (D) TOPOLOGY: linear (ii) MOLECULE TYPE: peptide (xi) SEQUENCE DESCRIPTION: SEQ ID NO: 26:

Cys Xaa His Xaa Xaa Cys Xaa Xaa Cys Xaa
1               5                   10

(2) INFORMATION FOR SEQ ID NO: 27:

(i) SEQUENCE CHARACTERISTICS:
        (A) LENGTH: 14 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 27:

Gly Xaa Xaa Xaa Gly Xaa Cys Xaa Cys Xaa Xaa Cys Xaa Cys
1               5                   10

(2) INFORMATION FOR SEQ ID NO: 28:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 28:

NUGYNNNNNN UGY                                                        13

(2) INFORMATION FOR SEQ ID NO: 29:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 29:

RCANNNNNRC A                                                          11

(2) INFORMATION FOR SEQ ID NO: 30:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 30:

GGAATTCRCA NNNCTGATGA GTCCGTGAG                                       29

(2) INFORMATION FOR SEQ ID NO: 31:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 31:

```
GGATCCNTGY NTTTCGTCCT CACGGACTCA                                                30
```

(2) INFORMATION FOR SEQ ID NO: 32:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 32:

```
UGYNNNNNNU GY                                                                   12
```

(2) INFORMATION FOR SEQ ID NO: 33:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 33:

```
NUGYNUNNNN UGY                                                                  13
```

(2) INFORMATION FOR SEQ ID NO: 34:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 34:

```
AGCTTRCANN NCTGATGAGT CCGTGAGGAC GAAANRCANA T                                   41
```

(2) INFORMATION FOR SEQ ID NO: 35:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 35:

```
CGATNTGYNT TTCGTCCTCA CGGACTCATC AGNNNTGYA                                      39
```

(2) INFORMATION FOR SEQ ID NO: 36:

(i) SEQUENCE CHARACTERISTICS:
        (A) LENGTH: 5 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 36:

```
Xaa Asn Xaa Val Asn
1               5
```

(2) INFORMATION FOR SEQ ID NO: 37:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 37:

NAAYNUNGUN AAY                                             13

(2) INFORMATION FOR SEQ ID NO: 38:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 38:

RUUNACCUGA UGAGUCCGUG AGGACGAAAN RUUN                   34

(2) INFORMATION FOR SEQ ID NO: 39:

(i) SEQUENCE CHARACTERISTICS:
        (A) LENGTH: 14 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 39:

Cys Xaa Xaa Xaa Gly Xaa Cys Xaa Cys Xaa Xaa Cys Xaa Cys
1              5                    10

(2) INFORMATION FOR SEQ ID NO: 40:

(i) SEQUENCE CHARACTERISTICS:
        (A) LENGTH: 5 amino acids
        (B) TYPE: amino acid
        (C) STRANDEDNESS: not relevant
        (D) TOPOLOGY: linear (ii) MOLECULE TYPE: peptide (xi) SEQUENCE DESCRIPTION: SEQ ID NO: 40:

Gly Xaa Cys Xaa Cys
1              5

(2) INFORMATION FOR SEQ ID NO: 41:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 41:

GNNNNUGYNN NUG                                               13

(2) INFORMATION FOR SEQ ID NO: 42:

```
        (i) SEQUENCE CHARACTERISTICS:
             (A) LENGTH: 34 base pairs
             (B) TYPE: nucleic acid
             (C) STRANDEDNESS: single
             (D) TOPOLOGY: linear (ii) MOLECULE TYPE: other nucleic acid (xi) SEQUENCE DESCRIPTION: SEQ ID NO: 42:

CANNNRCTGA TGAGTCCGTG AGGACGAAAN NNNC                                             34

(2) INFORMATION FOR SEQ ID NO: 43:

(i) SEQUENCE CHARACTERISTICS:
             (A) LENGTH: 4 amino acids
             (B) TYPE: amino acid
             (C) STRANDEDNESS: not relevant
             (D) TOPOLOGY: linear (ii) MOLECULE TYPE: peptide (xi) SEQUENCE DESCRIPTION: SEQ ID NO: 43:

Cys Xaa Xaa Cys
1

(2) INFORMATION FOR SEQ ID NO: 44:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: other nucleic acid (xi) SEQUENCE DESCRIPTION: SEQ ID NO: 44:

ATCCGCGTCC TAGGCACGTG A                                                          21

(2) INFORMATION FOR SEQ ID NO: 45:

(i) SEQUENCE CHARACTERISTICS:
             (A) LENGTH: 21 base pairs
             (B) TYPE: nucleic acid
             (C) STRANDEDNESS: single
             (D) TOPOLOGY: linear (ii) MOLECULE TYPE: other nucleic acid (xi) SEQUENCE DESCRIPTION: SEQ ID NO: 45:

GTTACTAGTC CGCGGCTCGA C                                                          21
```